US006441161B1

(12) United States Patent
Kirschenheuter et al.

(10) Patent No.: US 6,441,161 B1
(45) Date of Patent: Aug. 27, 2002

(54) UREA NUCLEOSIDES AS THERAPEUTIC AND DIAGNOSTIC AGENTS

(75) Inventors: Gary P. Kirschenheuter, Arvada; Bruce Eaton, Boulder, both of CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 09/707,253

(22) Filed: Nov. 6, 2000

Related U.S. Application Data

(60) Continuation of application No. 09/405,932, filed on Sep. 27, 1999, now Pat. No. 6,143,882, which is a division of application No. 08/622,772, filed on Mar. 27, 1996, now Pat. No. 5,959,100.

(51) Int. Cl.[7] ............................................. C07H 19/00

(52) U.S. Cl. ................. 536/27.1; 536/27.11; 536/27.3; 536/27.8; 536/27.81; 536/28.1; 536/28.5

(58) Field of Search ............................ 536/27.1, 27.11, 536/27.3, 27.8, 27.81, 28.1, 28.5

(56) References Cited

U.S. PATENT DOCUMENTS

| | | | |
|---|---|---|---|
| 4,415,732 A | 11/1983 | Caruthers et al. | |
| 4,725,677 A | 2/1988 | Köster et al. | |
| 4,904,582 A | 2/1990 | Tullis | |
| 4,923,901 A | 5/1990 | Koester et al. | |
| 4,948,882 A | 8/1990 | Ruth | |
| 5,023,243 A | 6/1991 | Tullis | |
| 5,047,519 A | 9/1991 | Hobbs, Jr. et al. | |
| 5,053,499 A | 10/1991 | Kojima et al. | |
| 5,118,672 A | 6/1992 | Schinazi et al. | |
| 5,118,802 A | 6/1992 | Smith et al. | |
| 5,134,066 A | 7/1992 | Rogers et al. | |
| 5,138,045 A | 8/1992 | Cook et al. | |
| RE34,069 E | 9/1992 | Köster et al. | |
| 5,420,276 A | 5/1995 | Norbeck | |
| 5,428,149 A | 6/1995 | Eaton | |
| 5,580,972 A | 12/1996 | Tu et al. | |
| 5,959,100 A | * 9/1999 | Kirschenheuter et al. | |
| 6,143,882 A | * 11/2000 | Kirschenheuter et al. | |

FOREIGN PATENT DOCUMENTS

| | | |
|---|---|---|
| WO | WO 90/15065 | 12/1990 |
| WO | WO 91/06556 | 5/1991 |
| WO | WO 91/06629 | 5/1991 |
| WO | WO 91/10671 | 7/1991 |
| WO | WO 91/14696 | 10/1991 |
| WO | WO 94/26761 | 11/1994 |

OTHER PUBLICATIONS

Agathocleous and Shaw (1991) J. Chem. Soc. Perkin Trans. 1 10:2317.
Albano and Castellari (1990) Organometallics 9:1269.
Arai et al. (1978) J. Am. Chem. Soc. 100:287.
Baillargeon and Stille (1983) J. Am. Chem. Soc. 105:7175.
Bergstrom et al. (1982) J. Org. Chem. 47:2174.
Bergstrom et al. (1981) J. Org. Chem. 46:1432.
Bergstrom et al. (1976) J. Am. Chem. Soc. 98:1587.
Bigge and Mertes (1981) J. Org. Chem. 46:1994.
Brown and Cooley (1990) Organometallics 9:353.
Cadet and Teoule (1978) Photochemistry and Photobiology 28:661.
Cadet and Teoule (1974) Bull. Soc. Chim. 7:1565.
*Comp. Organomet. Chem.* (1982) 6:1003, Wilkinson, Stone & Abel, Editors, Pergamon Press.
Crisp (1989) Synthetic Communications 19:2117.
Crisp and Flynn (1990) Tetrahedron Letters 31:1347.
Crouch and Eaton (1994) Nucleosides & Nucleotides 13:939.
de Graaf et al. (1990) Organometallics 9:1479.
Dreyer and Dervan (1985) Proc. Natl. Acad. Sci. USA 82:968.
Englisch and Gauss (1991) Angew. Chem. Int. Ed. Engl. 30:613.
Fukuda et al. (1986) Z. Naturforsch. 41b:1571.
Girault et al. (1994) Free Rad. Res. 20:315.
Guschlbauer et al. (1977) Nucleic Acids Res. 4:1933.
Hacksell and Daves (1983) J. Org. Chem. 48:2870.
Hobbs et al. (1973) Biochemistry 12:5138.
Hung and Stock (1982) J. Org. Chem. 47:448.
Iida and Hayatsu (1971) Biochimica et Biophysica Acta 228:1.
Ikehara and Tada (1968) *Synthetic Procedures in Nucleic Acid Chemistry*, Zorbach, W.W.; Tipson, R.S. Eds.; John Wiley and Sons, NY p. 189.

(List continued on next page.)

*Primary Examiner*—James O. Wilson
(74) *Attorney, Agent, or Firm*—Swanson & Bratschun, L.L.C.

(57) ABSTRACT

Modified nucleosides and methods of making and using the nucleosides are disclosed. The compounds can be prepared by reacting nucleoside starting materials that contain a suitable leaving group at one or more of the carbon atoms in the purine or pyrimidine ring, with a vinylstannane, carbon monoxide, and a palladium catalyst to provide 1-ene-3-one intermediates. These intermediates are then reacted with suitably functionalized primary or secondary amines via a Michael reaction. When the intermediate is a 5-position modified pyrimidine ring, and the amine contains a second hydrogen, it can do a second Michael reaction with the ene-one or the ene-imine in the pyrimidine ring. Appropriate modification of the amine reactant can yield products with various bioactivities. The nucleosides can be used therapeutically as anti-cancer, anti-bacterial or anti-viral drugs. The nucleosides can also be used for diagnostic applications, for example, by incorporating a radiolabel or fluorescent label into the molecule. The nucleosides can be used to prepare oligonucleotides for use in various applications, either alone or in combination with other modified nucleosides and/or naturally occurring nucleosides.

3 Claims, No Drawings

OTHER PUBLICATIONS

Ono et al. (1994) Bioorg. & Med. Chem. Lett. 4:361.
Pieken et al. (1991) Science 253:314.
Ross et al. (1994) J. Heterocyclic Chem. 31:765.
Ruth and Bergstrom (1978) J. Org. Chem. 43:2870.
Sagi et al. (1994) J. Med. Chem. 37:1307.
Scott and Stille (1986) J. Am. Chem. Soc. 108:3033.
Sentemov et al. (1991) Chemical Abstracts 115:92415h.
Sessler et al. (1993) J. Am. Chem. Soc. 115:10418.
Shibahara et al. (1987) Nucleic Acids Res. 15:4403.
Sproat et al. (1989) Nucleic Acids Res. 17:3373.
Stille (1986) Angew. Chem. Int. Ed. Engl. 25:508.
Stille and Groh (1987) J. Am. Chem. Soc. 109:813.
Thiesen and Bach (1990) Nucleic Acids Res. 18:3203.
Tronchet et al. (1988) Nucleosides & Nucleotides, 7:249.
Tronchet et al. (1990) Tetrahedron Letters 31:531.
Van Aerschot et al. (1993) J. Med. Chem. 36:2938.
Yamamoto et al. (1989) J. Org. Chem. 54:4734.
Zhang et al. (1993) Organometallics 12:1499.

* cited by examiner

UREA NUCLEOSIDES AS THERAPEUTIC AND DIAGNOSTIC AGENTS

RELATED APPLICATIONS

This application is a continuation application of U.S. application Ser. No. 09/405,932, filed Sep. 27, 1999, now U.S. Pat. No. 6,143,882, which is a divisional of U.S. application Ser. No. 08/622,772, filed Mar. 27, 1996, now U.S. Pat. No. 5,959,100.

FIELD OF THE INVENTION

This invention is in the field of modified nucleosides, and in particular, in the field of modified nucleosides for use in diagnostic applications and as therapeutic agents.

BACKGROUND OF THE INVENTION

There has been considerable interest in developing modified nucleosides as therapeutic agents, diagnostic agents, and for incorporation into oligonucleotides. For example, modified nucleosides such as AZT, ddI, d4T, and others have been used to treat AIDS. 5-trifuoromethyl-2'-deoxyuridine is active against herpetic keratitis and 5-iodo-1-(2-deoxy-2-fluoro-b-D-arabinofuranosyl)cytosine has activity against CMV, VZV, HSV-1, HSV-2 and EBV (A Textbook of Drug Design and Development, Povl Krogsgaard-Larsen and Hans Bundgaard, Eds., Harwood Academic Publishers, 1991, Ch. 15).

Modified nucleosides have shown utility in diagnostic applications. In these applications, the nucleosides are incorporated into DNA in determinable locations, and various diagnostic methods are used to determine the location of the modified nucleosides. These methods include radiolabeling, fluorescent labeling, biotinylation, and strand cleavage. An example of strand cleavage involves reacting the nucleoside with hydrazine to yield urea nucleosides, then reacting the urea nucleoside with piperidine to cause strand cleavage (the Maxam-Gilbert method).

Modified nucleosides have also been incorporated into oligonucleotides. There are several ways in which oligonucleotides may be useful as therapeutics. Antisense oligonucleotides can bind certain genetic coding regions in an organism to prevent the expression of proteins or to block various cell functions. Further, a process known as the SELEX process, or Systematic Evolution of Ligands for EXponential Enrichment, allows one to identify and produce oligonucleotides that selectively bind target molecules. The SELEX process is described in U.S. Pat. No. 5,270,163 issued Dec. 14, 1993, entitled "Methods for Identifying Nucleic Acid Ligands,". the contents of which are hereby incorporated by reference.

The SELEX method involves the selection of oligonucleotides from a mixture of candidates to achieve virtually any desired criterion of binding affinity and selectivity. Starting from a random mixture of oligonucleotides, the method involves contacting the mixture with a target under conditions favorable for binding (or interacting), partitioning unbound oligonucleotides from oligonucleotides which have bound to (or interacted with) target molecules, dissociating the oligonucleotide-target pairs, amplifying the oligonucleotides dissociated from the oligonucleotide-target pairs to yield a ligand-enriched mixture of oligonucleotides, then reiterating the steps of binding, partitioning, dissociating and amplifying through as many cycles as desired.

Modified nucleosides can be incorporated into antisense oligonucleotides, ribozymes, and oligonucleotides used in or identified by the SELEX process. These nucleosides can impart in vivo and in vitro stability of the oligonucleotides to endo and exonucleases, alter the charge, hydrophilicity or lipophilicity of the molecule, and/or provide differences in three dimensional structure.

Modifications of nucleosides that have been previously described include 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, and methylations. Modifications have also included 3' and 5' modifications such as capping. PCT WO 91/14696, incorporated herein by reference, describes a method for chemically modifying antisense oligonucleotides to enhance entry into a cell.

U.S. Pat. No. 5,428,149 to Eaton, which is incorporated herein in its entirety, describes modifying pyrimidine nucleosides via a palladium coupling reaction in which a nucleophile and carbon monoxide are coupled to pyrimidine nucleosides containing a leaving group on the 5-position of the pyrimidine ring, preferably forming ester and amide derivatives.

A variety of methods have been used to render oligonucleotides resistant to degradation by exonucleases. PCT WO 90/15065 describes a method for making exonuclease-resistant oligonucleotides by incorporating two or more phosphoramidate, phosphoromonothionate and/or phosphorodithionate linkages at the 5' and/or 3' ends of the oligonucleotide. PCT WO 91/06629 discloses oligonucleotides with one or more phosphodiester linkages between adjacent nucleosides replaced by forming an acetal/ketal type linkage which is capable of binding RNA or DNA.

RNA has been stabilized against endonucleolytic cleavage by modifying the 2'-position of the ribonucleosides. One approach to stabilization against base-specific endonucleolytic cleavage rests on the interference with base recognition by enzymes. Several strategies for this modification are known, including modification with 2'-amino and 2'-fluoro (Hobbs et al., Biochemistry, 12:5138 (1973), Guschlbauer et al., Nucleic Acid Res. 4:1933 (1977)), and 2'-OCH$_3$ (Shibahara et al., 15:4403 (1987); Sproat et al., Nucleic Acids Res., 17:3373 (1989), each of which is hereby incorporated by reference). PCT WO 91/06556, also incorporated by reference, describes nuclease-resistant oligomers with substituents at the 2'-position. PCT WO 91/10671 describes antisense oligonucleotides chemically modified at the 2'-position and containing a reactive portion capable of catalyzing, alkylating, or otherwise affecting the cleavage of RNA, a targeting portion, and a tether portion for connecting the targeting and reactive portions.

It would be advantageous to provide new nucleosides for therapeutic and diagnostic applications and for inclusion in oligonucleotides. When incorporated in oligonucleotides, it would be advantageous to provide new oligonucleotides that exhibit different high affinity binding to target molecules, and/or show increased resistance to exo and endonucleases than oligonucleotides prepared from naturally occurring nucleosides. It would also be useful to provide nucleotides with modifications that impart a biological activity other than, or in addition to, endo and exonuclease resistance.

It is therefore an object of the present invention to provide modified nucleosides that are useful for therapeutic administration and/or diagnostic applications.

It is a further object of the present invention to provide modified nucleosides that are useful for incorporation into oligonucleotides to allow for binding to or otherwise interacting with target molecules that may be different than would be obtained if naturally occurring nucleosides were used.

It is still a further object of the present invention to provide nucleosides with modifications that may impart a biological activity other than, or in addition to, endo and exonuclease resistance. It is yet a further object of the present invention to provide novel methods for preparing modified nucleosides.

SUMMARY OF THE INVENTION

Novel compounds which are useful as diagnostic agents and as antitumor, antiviral and/or antibiotic therapeutic agents, and methods of preparation and use thereof, are disclosed. The compounds are modified nucleosides, specifically pyrimidine and purines, where the modifications are at the 5- or 6-position of a pyrimidine ring or at the 2-, 6- or 8-positions of the purine ring. Most preferably, the modifications are at the 5-position of the pyrimidine ring and at the 8-position of the purine ring. Although naturally occurring purine nucleosides contain an amine (or carbonyl) group at the 6-position, the amine group can be diazotized and replaced with a halogen using routine chemistry.

The modified purine compounds of the invention are structurally illustrated by formulae (I) and (II) and the modified pyrimidine compounds are structurally illustrated by formulae (III) and (IV), below. The modified urea nucleosides of the present invention are illustrated by formulae (V) and (VI).

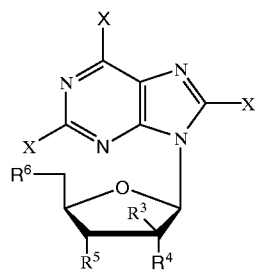

I

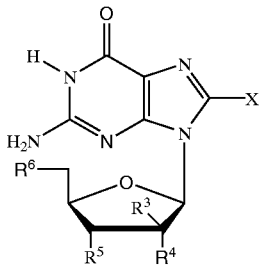

II

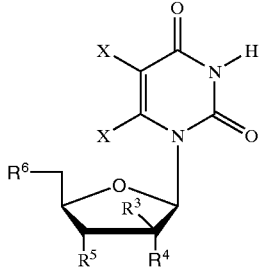

III

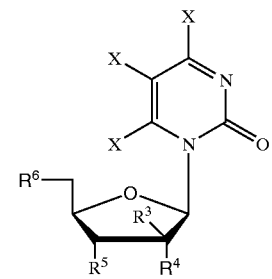

IV

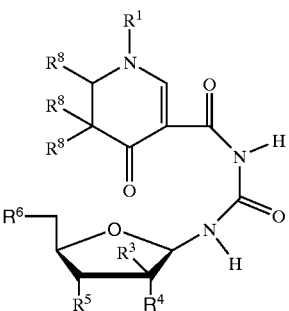

V

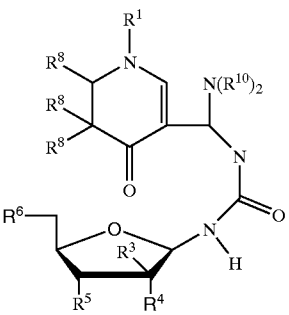

VI wherein:
X is independently selected from the group consisting of H aryl, aralkyl alkyl, alkaryl, alkenyl, alkynyl, alkoxy, —$NR^{10}{}_2$, and $C(O)CH(R^8)C(R^8)_2NR^1R^2$, and wherein at least one of X is $C(O)CH(R^8)C(R^8)_2NR^1R^2$, $R^1$ and $R^2$ are independently selected from the group consisting of H, $C_1$–$C_{18}$ alkyl, alkenyl or alkynyl, phenyl, aralkyl, alkaryl, an alkanoic acid or its ester and amide derivatives, a peptide fragment which possesses a specified function (i.e., an enzyme inhibitor, receptor antagonist, receptor agonist, etc.), an HIV aspartyl protease inhibitor, groups that are cleaved intracellularly, and groups that increase the hydrophilicity, hydrophobicity, electrostatic capacity or hydrogen bonding capacity of the compound;

$R^3$, $R^4$ and $R^5$ are independently selected from the group consisting of H, —OH, protected oxy-, —$NH_2$, F, —$N_3$, —CN, —NC, —OAc, —SAc, —OBz, and —$OSiR^7{}_3$, wherein $R^7$ is $C_1$–$C_4$ alkyl or phenyl;

$R^6$ is selected from the group consisting of —OH, protected oxy-, phosphate, diphosphate, triphosphate, phosphate esters, phosphoramidites, phosphorothionates, and phosphorodithionates;

$R^8$ is independently selected from the group consisting of H, aryl, aralkyl, alkyl, alkaryl, alkenyl, alkynyl, alkoxy, trialkyl silyl, dialkylaryl silyl, alkyldiaryl silyl, triarylsilyl, and —C(O)—$R^9$, where $R^9$ is selected from the group consisting of H, alkyl, aryl, aralkyl, alkaryl and alkoxy;

$R^{10}$ is independently selected from the group consisting of H, alkyl, aryl, aralkyl, alkaryl and $R^9C(O)$;

the protected oxy- groups of $R^4$ and $R^5$ taken together can represent an isopropylidene group (—OC(CH$_3$)$_2$O—) or an orthoformate group (—OCH(OR$^7$)O—); and the protected oxy- groups of $R^5$ and $R^6$ taken together can represent a 3',-5'-tetraalkyldisiloxane group (—OSi(alkyl)$_2$OSi(alkyl)$_2$O—).

The general process used to prepare the modified purines and pyrimidines is shown below in Scheme I using cytidine and guanine starting materials. As shown in the scheme, the process includes reacting a nucleoside with a suitable leaving group with a palladium catalyst in conjunction with a vinylstannane and carbon monoxide to provide an ene-one functionalized nucleoside intermediate. The intermediate is then reacted with a functionalized amine containing the desired $R^1$ and $R^2$ groups in a Michael addition reaction. When primary amines (or secondary amines that contain a cleavable functional group) are added to a pyrimidine ring with an ene-one at the 5-position, the amine is capable of a second Michael addition reaction that adds to the ene-one or ene-imine in the pyrimidine ring. When an ene-one functionality is introduced at the 2-, 6- or 8-position of a purine ring, and a primary amine is added via a Michael addition reaction, the purine ring system is not capable of participating in a second Michael addition reaction.

Scheme I

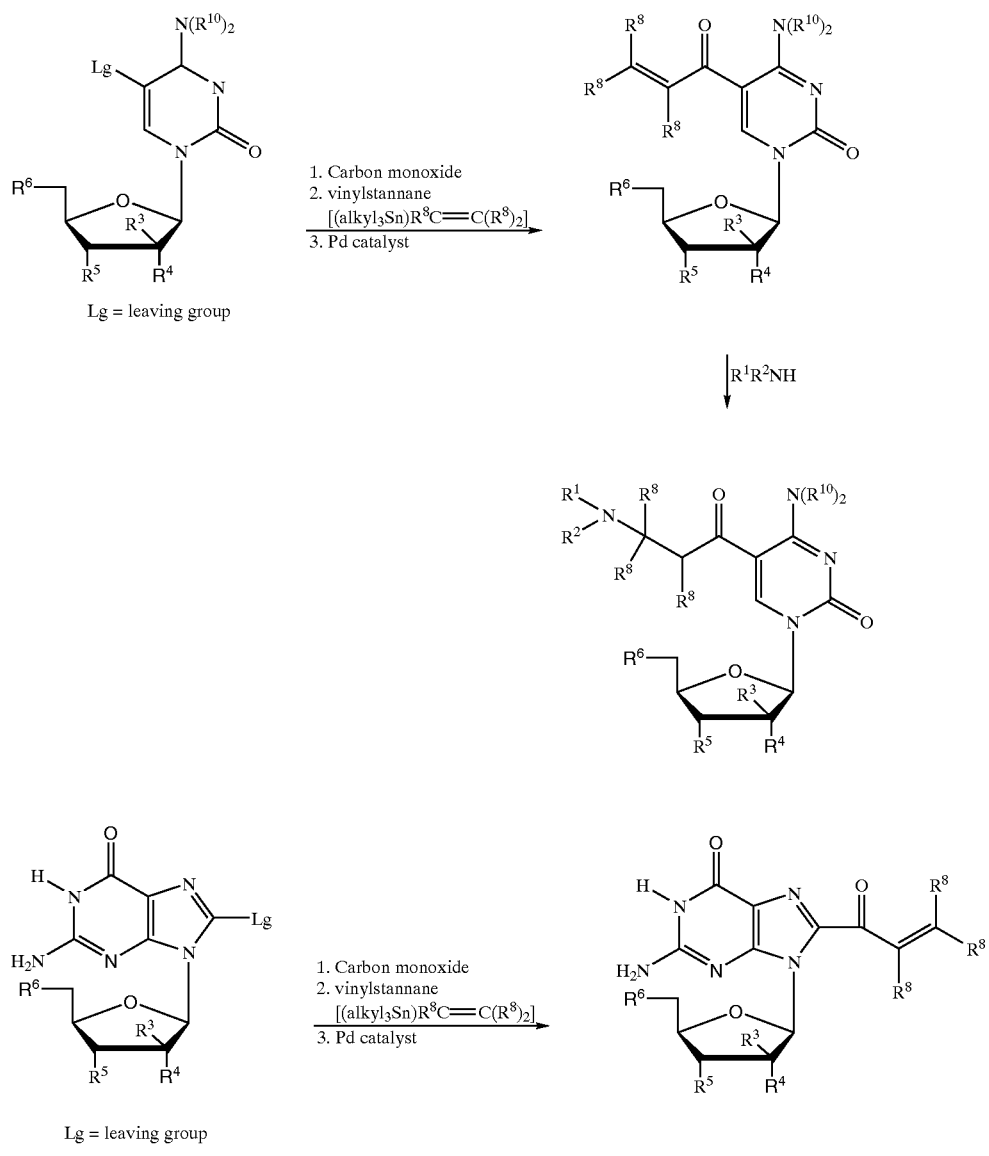

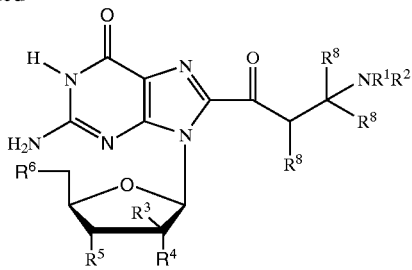

Depending one the starting compound, the functional group at any or all of positions $R^3$–$R^6$ can be hydroxy groups. Any or all of these hydroxy groups can be protected, or not, depending on the intended use of the resulting products. The protecting group can be any protecting group suitable for use with hydroxyl groups. Suitable protecting groups include, but are not limited to, isopropylidene ketals, tetraisopropyldisiloxyl (TIPS) ethers, t-butyldimethylsilyl (TBDMS), t-butyldiphenylsilyl, methoxymethyl (MOM), methoxyethoxymethyl (MEM), tetrahydropyranyl (THP), triphenylmethyl (Tr), monomethoxytrityl (MTr), and dimethoxytrityl (DMTr).

The intermediate containing the 3-ene-1-one moiety is a key intermediate which can be used to synthesize a number of compounds of the invention. In the case of pyrimidines with a leaving group at the 5-position, treating the intermediate with primary amines (as the free base or as the hydrochloride salt in the presence of an organic base) forms the urea nucleoside derivatives of Formulae V and VI. Alternatively, secondary amines can react with the 3-ene-1-one intermediates to give the nucleoside derivatives of Formulae I–IV. The chemistry described in steps a and b is described in U.S. Pat. No. 5,428,149 to Eaton, the contents of which are hereby incorporated by reference.

In one embodiment, the 5'- and 3'-hydroxy groups in nucleoside derivatives with a suitable leaving group at the 5-position can be protected with a tetraisopropyldisiloxyl (TIPS) group to gain access to "free" nucleoside analogs. These compounds undergo the above-described palladium catalyzed conversion in good yield to provide the TIPS protected intermediates.

In another embodiment, $R^1$ and $R^2$ are chosen to modulate, modify and/or control the biological activity of the compound, whether the compound is used alone or incorporated into an oligonucleotide. This can be achieved by adding a second biological activity to the compound, and/or enhancing the efficacy, bioavailability, potency, specificity and/or limits the toxicity of the compound. For example, aspartyl protease inhibitors and 3'-azides such as AZT function differently. Protease inhibitors function by inhibiting aspartyl protease activity, and 3'-azide groups function by inhibiting DNA replication. By choosing $R^1$ or $R^2$ to be an HIV aspartyl protease inhibitor and $R^5$ to be $N_3$, one can provide a dual action antiviral for treating HIV infection.

According to a further aspect of the invention, when one of $R^1$ or $R^2$ is H, the compounds of the formulae (III) or (IV) can undergo rearrangement to the compounds of formulae (V) or (VI), respectively. By choosing $R^1$ or $R^2$ as a group which is cleaved intracellularly (or in the nucleus of the cell) one can prepare nucleotides of the formulae (III) or (IV) which incorporate into viral DNA or RNA as nucleotide analogs, and then subsequently rearrange to the corresponding urea derivatives upon cleavage of $R^2$ to H, thereby disrupting the genetic information of the pathogen. Examples of such groups include, but are not limited to,

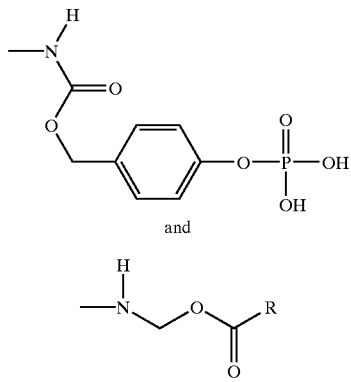

In addition, in any of the modified nucleosides, $R^1$ and $R^2$ can be chosen to increase either the lipophilicity (i.e., alkyl groups larger than about $C_{18}$, tertiary alkylamines, and polyethylene glycol fragments) or the hydrophilicity (i.e., carboxylates, phosphates, sulfonates, ammonium-salts, particularly quaternary ammonium salts, hydroxy groups, and thiols) of the compounds in order to optimize their bioavailability.

The nucleosides can also be modified such that they contain one or more radiolabels. Suitable radiolabels include, but are not limited to, $^{14}C$, $^{32}P$, $^{3}H$, $^{131}H$, $^{35}S$, $^{18}O$, and $^{19}F$. These radiolabels can be incorporated into the nucleoside by means known to those of skill in the art. The nucleosides can also contain fluorescent labels, such as rhodamine or fluorescein, and/or can be biotinylated. When modified in this fashion, the nucleosides are particularly useful as in vivo or in vitro diagnostic agents.

The modified nucleosides may be useful therapeutically, to treat viral infections, bacterial infections, and/or cancer. Embodiments in which $R^2$ is a group that can be cleaved intracellularly can be incorporated into DNA, and then cleaved intracellularly in vivo to affect DNA replication. The nucleosides can also be used in diagnostic applications, where they are incorporated into DNA in determinable locations, and the location is determined by a suitable diagnostic method. Further, the nucleosides can contain radiolabels, fluorescent tags and/or be biotinylated such that they can be detected after they are incorporated into DNA.

Oligonucleotides can be prepared that are made solely from the modified nucleosides, or that include other modified nucleosides and/or naturally occurring nucleosides. Oligonucleotides prepared in this fashion can be used, for example, as antisense oligonucleotides, ribozymes, or as nucleic acid ligands described in the SELEX process to bind to or interact with specific target sites.

DETAILED DESCRIPTION OF THE INVENTION

Definitions

As used herein, the term "nucleoside starting material" is defined as any nucleoside base, nucleoside or nucleotide that has an attached acceptable leaving group. Nucleoside starting materials include all nucleosides, both naturally occurring and non-naturally occurring. Preferably, nucleoside starting materials include purines and pyrimidines, which include uracil, thymine, cytosine, adenine, and guanine starting materials. The leaving group can be attached to any free carbon on the nucleoside base. The acceptable leaving group is displaced during the palladium coupling reaction and replaced with an ene-one moiety. The resulting intermediate is reacted with a suitable amine to provide the modified nucleosides of the present invention.

As used herein, the term "pyrimidine starting material" is defined as a pyrimidine base, pyrimidine nucleoside or pyrimidine nucleotide that has an attached acceptable leaving group. Pyrimidine starting materials include all pyrimidines, both naturally occurring and non-naturally occurring. Preferably, pyrimidine starting materials include uracil, thymine, and cytosine with attached leaving groups. The leaving group can be attached to any free carbon on the nucleoside, preferably at the 5- or 6-position. The most preferred attachment is at the 5-position.

As used herein, the term "purine starting material" is defined as a purine base, purine nucleoside or purine nucleotide that has an attached acceptable leaving group. Purine starting materials include all purines, both naturally occurring and non-naturally occurring. Preferably, purine starting materials include adenine and guanine with attached leaving groups. The leaving group can be attached to any free carbon on the nucleoside, preferably at the 2-, 6-or 8-position. The most preferred attachment is at the 8-position.

As used herein, the term "palladium catalyst" is defined as any palladium catalyst capable of coupling a purine or pyrimidine ring, a vinyl stagnate and carbon monoxide to form an ene-one modified purine or pyrimidine nucleoside. Suitable catalysts for performing the coupling reaction include, but are not limited to $PAL_3$ and $PAL_4$, where L is any ligand normally associated with palladium. The preferred catalyst for the coupling reaction is $Pd[P(pH)_3]_3$. Catalysts including mixtures of $Pd[P(pH)_3]_3$ and $Pd(OAc)_2$ are also suitable for practicing the present invention. When $Pd(P(pH)_3)_3$ and $Pd(OAc)_2$ are employed together, the preferred molar ratio is about 3:1 $Pd(P(pH)_3)_3$ to $Pd(OAc)_2$. In a preferred embodiment, the catalyst also includes CUE.

As used herein, the term "acceptable leaving group" is defined as a group that is a suitable counterion for palladium II. In the most general embodiments of the present invention, the leaving group is any of a number of acceptable leaving groups known to those of skill in the art. Acceptable leaving groups include, but are not limited to, halogens, acetate, trifluoroacetate, trifluoromethyl sulfonate, tosylate, methane sulfonate, and boronic esters and acids. Preferably, the leaving group is a halogen, and, more preferably, the leaving group is iodide or bromide.

As used herein, the term "alkyl" is defined as a $C_{1-18}$ straight, branched or cyclic alkane. Preferably, the alkyl groups are between $C_1$ and $C_{10}$, and, more preferably, between $C_1$ and $C_6$.

As used herein, the term "alkenyl" is defined as a $C_{2-18}$ straight or branched alkene, or a $C_{5-18}$ cyclic alkene. Preferably, the alkenyl groups are between $C_2$ and $C_{10}$, and, more preferably, between $C_2$ and $C_6$.

As used herein, the term "alkynyl" is defined as a $C_{2-18}$ straight or branched alkyne, or a $C_{8-18}$ cyclic alkyne. Preferably, the alkynyl groups are between $C_2$ and $C_{10}$, and, more preferably, between $C_2$ and $C_6$.

As used herein, the term "aryl" is defined as a $C_6$–$C_{10}$ aromatic ring system.

As used herein, the term "alkoxy" as defined as a $C_1$–$C_{18}$ straight or branched ether.

As used herein, the term "aralkyl" is defined as an aryl ring functionalized with one or more alkyl groups.

As used herein, the term "alkaryl" is defined as an alkyl substituent functionalized with an aryl ring.

As used herein, the term "alkanoic acid" is defined as a $C_{1-18}$ straight or branched alkane, or a $C_{5-18}$ cyclic alkane, containing a carboxylic acid functionality.

As used herein, the term "enzyme inhibitor" is defined as a moiety that inhibits the function of an enzyme.

As used herein, the term "receptor antagonist" is defined as a moiety that inhibits binding to or interacting with a receptor.

As used herein, the term "receptor agonist" is defined as a moiety that assists in binding to or interacting with a receptor.

As used herein, the term "modified nucleoside" is defined as a non-naturally occurring nucleoside, and specifically includes uridine, cytidine, adenine and guanine derivatives, as well as the urea nucleoside derivatives. The modified nucleosides of the present invention include at least one moiety of the formula $C(O)CH(R^8)C(R^8)_2NR^{12}$, where $R^1$, $R^2$ and $R^8$ are as defined below.

As used herein, the term "vinylstannane" is defined as $(alkyl_3Sn)(R^8)C=C(R^8)_2$, wherein alkyl is preferably n-butyl, and $R^8$ is, independently, selected from the group consisting of H, aryl, aralkyl, alkyl, alkaryl, alkenyl, alkynyl, alkoxy, trialkyl silyl, dialkylaryl silyl; alkyldiaryl silyl, triarylsilyl, and —C(O)—$R^9$, where $R^9$ is selected from the group consisting of H, alkyl, aryl, aralkyl, alkaryl and alkoxy.

As used herein, the term "protecting group" is defined as a functional group that protects a certain functionality in a molecule from undesired reactions during a chemical reaction on another part of the molecule, but that can be easily removed to provide the original functional group. Examples of protecting groups are well known to those of skilled in the art, and are taught, for example, in Greene and Wuts, "Protective Groups in Organic Chemistry," 2d Ed., John Wiley and Sons, N.Y. (1991).

Protecting groups for hydroxy groups include, but are not limited to, ketals, such as the isopropylidene ketal, silyl ethers, such as TIPS ethers, tetrahydropyranyl ethers, methyl ethers, benzyl ethers, and t-butyl ethers.

Protecting groups for phosphate groups include, but are not limited to, benzyl, 2-cyanoethyl, 2-(4-nitrophenyl)ethyl, and 2-trimethylsilylethyl.

Protecting groups for amine groups include, but are not limited to, di-t-butoxycarbonyl (t-Boc), fluorenyloxycarbonyl (Fmoc) and carbobenzoxy (CBz) groups.

Protecting groups for thiols include, but are not limited to, thioketals, benzyl thioethers, silyl thioethers, trityl thioethers, disulfides, and thioesters.

As used herein, an "HIV aspartyl protease inhibitor" is defined as groups that inhibit HIV 1 aspartyl protease or HIV2 aspartyl protease. Suitable examples include. but are not limited to, $-CH_2CH_2C(OH)(pH)CH_2CH,-$, —CH$_2$CH$_2$C(OH)(4-ClPh)CH$_2$CH$_2$—, —CH,CH$_2$C(OH)(4-FPh)CH$_2$CH$_2$—,

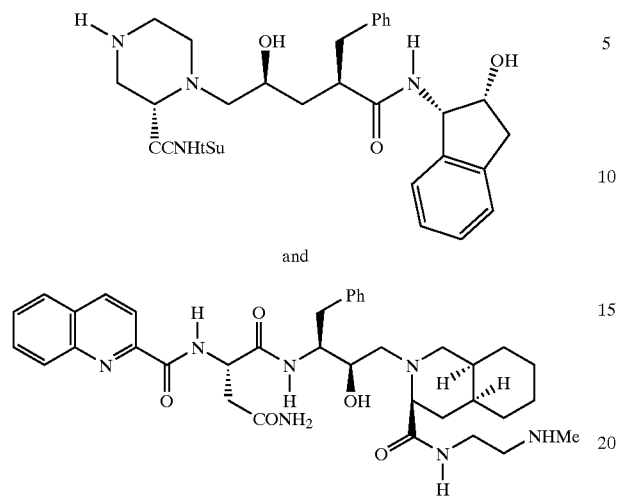

and where the arrows indicate points of attachment to the 3-ene-1-one intermediate in a Michael reaction, as discussed in detail below.

Functional groups that enhance the therapeutic efficacy and/or potency of the compound include, but are not limited to. free NH bonds, fluoro groups, azide groups, and isocyanate groups.

Functional groups that enhance the specificity of the compound include, but are not limited to, antibodies, protein fragments, active-site directed compounds, and non-nucleic acid components that fit into specific binding pockets to form a tight binding via appropriate hydrogen bonds, salt bridges, or van der Waals interactions.

Functional groups that increase the lipophilicity of the compound include, but are not limited to, alkyl groups larger than about C$_{18}$, tertiary alkylamines, and polyethylene glycol fragments.

Functional groups that increase the hydrophilicity of the compound include, but are not limited to, carboxylates, phosphates, sulfonates, ammonium salts, particularly quaternary ammonium salts, hydroxy groups, and thiols.

Modified nucleosides and methods of preparation and use thereof are disclosed. The modified nucleosides have the general formulae:

I

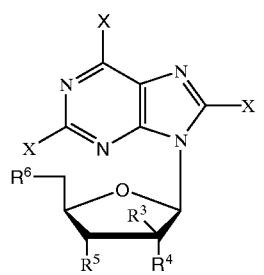

II

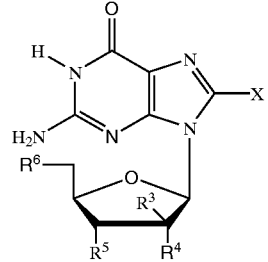

III

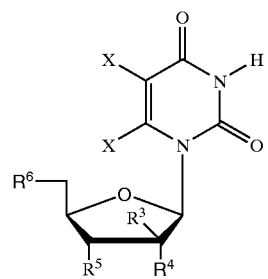

IV

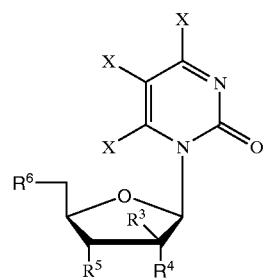

V

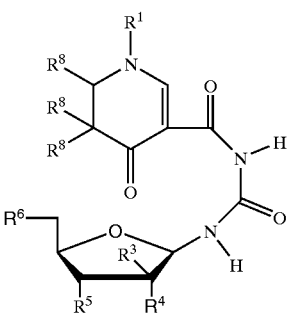

VI

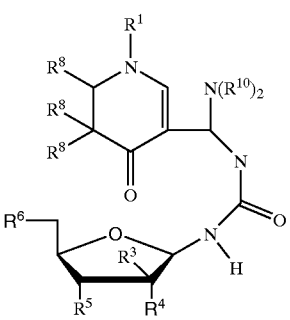

wherein:
X is independently selected from the group consisting of H aryl aralkyl, alkyl, alkaryl, alkenyl, alkynyl, alkoxy —NR$^{10}$$_2$, and C(O)C(R$^8$)$_2$C(R$^8$)NR$^1$R$^2$, and wherein at least one of X is C(O)CH(R$^8$)C(R$^8$)$_2$NR$^1$R$^2$.

R$^1$ and R$^2$ are independently selected from the group consisting of H, C$_1$–C$_{18}$ alkyl, alkenyl or alkynyl, phenyl, aralkyl, alkaryl, an alkanoic acid or its ester and amide derivatives, a peptide fragment which possesses a specified function (i.e., an enzyme inhibitor, receptor antagonist, receptor agonist, etc.), an HIV aspartyl protease inhibitor, groups that are cleaved intracellularly, and groups that increase the hydrophilicity, hydrophobicity, electrostatic capacity or hydrogen bonding capacity of the compound, $R^3$ through $R^5$ are independently selected from the group consisting of H, —OH, protected oxy-, —$NH_2$, F, —$N_3$, —CN, —NC, —OAc, —SAc, —OBz, and —$OSiR^7_3$, wherein $R^7$ is $C_1$–$C_4$ alkyl or phenyl;

$R^6$ is selected from the group consisting of —OH, protected oxy-, phosphate, diphosphate, triphosphate, phosphate esters, phosphoramidites, phosphorothionates, and phosphorodithionates;

$R^8$ is independently selected from the group consisting of H, aryl, aralkyl, alkyl, alkaryl, alkenyl, alkynyl, alkoxy, trialkyl silyl, dialkylaryl silyl, alkyldiaryl silyl, triarylsilyl, and —C(O)—$R^9$, where $R^9$ is selected from the group consisting of H, alkyl, aryl, aralkyl, alkaryl and alkoxy;

$R^{10}$ is independently selected from the group consisting of H, alkyl, aryl, aralkyl, alkaryl and $R^9$C(O);

the protected oxy- groups of $R^4$ and $R^5$ taken together can represent an isopropylidene group (—OC$(CH_3)_2$O—) or an orthoformate group (—OCH($OR^7$)O—); and the protected oxy- groups of $R^5$ and $R^6$ taken together can represent a 3',-5'-tetraalkyldisiloxane group (—OSi(alkyl)$_2$OSi(alkyl)$_2$O—).

The nucleosides can also be modified such that they contain one or more radiolabels. Suitable radiolabels include, but are not limited to, $^{14}C$, $^{32}P$, $^3H$, $^{131}I$, $^{35}S$, $^{18}O$, and $^{19}F$. These radiolabels can be incorporated into the nucleoside by means known to those of skill in the art. The nucleosides can also contain fluorescent labels, such as rhodamine or fluorescein, or can be biotinylated. These labels can be incorporated into the nucleoside by means known to those of skill in the art. When modified in this fashion, the nucleosides are particularly useful as in vivo or in vitro diagnostics.

Preparation of the Compounds of the Present Invention

The compounds of the invention can be prepared by a) optionally protecting one or more of the hydroxy groups in a nucleoside starting material that contains the desired $R^{3-6}$ groups, b) reacting the nucleoside starting material containing a leaving group attached to a carbon of the nucleoside starting material with a suitably substituted vinylstannane or other suitable compound and carbon monoxide in the presence of a palladium catalyst to replace the leaving group with a 3-ene-1-one moiety, and c) reacting the resulting 3-ene-1-one with an amine containing the desired $R^1$ and $R^2$ groups.

Preparing Nucleoside Derivatives with the Desired $R^{3-6}$ Groups

Preparation of modified nucleosides in general, and cytidine, uridine, guanine and adenine derivatives, in particular, is well known. Modifications of nucleosides that have been previously described include 2'-position sugar modifications, 5'-position pyrimidine modifications, 8-position purine modifications, modifications v at exocyclic amines, substitution of 4-thiouridine, substitution of 5-bromo or 5-iodo-uracil, backbone modifications, and methylations. Modifications have also included 3' and 5' modifications such as capping. PCT WO 91/14696 describes a method for chemically modifying antisense oligonucleotides to enhance entry into a cell.

The modified nucleosides can be prepared by means well known to those of skill in the art. A straightforward method for modifying nucleosides at the 2'-position involves protecting reactive functional groups on the base, and protecting the 3'- and 5'-hydroxy groups as the TIPS ethers. This allows functionalization of the 2'-hydroxy group using known chemistry that does not adversely affect the protecting groups. For example, the 2'-hydroxy group in a suitably protected nucleoside can be reacted with methyl iodide to form a methyl ether. Reaction with tosyl chloride or a similar compound to convert the hydroxy group to a suitable leaving group, followed by nucleophilic displacement with a desired nucleophile, can also provide a variety of substitutions at the 2'-position.

Modifications can be selectively performed at the 3'-position by selectively protecting the 2'- and 5'-positions, and performing the same chemistry indicated above. One method for selectively protecting the 2'- and 5'-positions is to protect the 3'- and 5'-positions as the TIPS ethers, protect the 2'-position with another protecting group, and remove the TIPS protecting groups, i.e., with fluoride ion. Then, the 5'-hydroxy group can be selectively protected, i.e., with a trityl group, leaving the 3'-hydroxy group available for subsequent modification.

Modifications can be selectively performed at the 5'-position by protecting the 5'-hydroxy group, then protecting the 2'- and 3'- hydroxy groups, i.e., as an isopropylidine ketal. The 5'-hydroxy group can then be selectively deprotected and reacted as described above.

Palladium Coupling Chemistry

The palladium coupling chemistry in step b) of the synthesis is described in detail in U.S. Pat. No. 5,428,149 to Eaton. Briefly, the hydroxy groups on a nucleoside starting material are optionally protected. The protected or unprotected nucleoside starting material is combined with a vinylstannane or other suitable compound and carbon monoxide in the presence of a suitable palladium catalyst.

Halogen leaving groups, particularly iodo or bromo derivatives, are preferred for the coupling chemistry. However, nucleoside derivatives with other leaving groups, such as trifluoroacetate, tifluoromethyl sulfonate, and boronic acids and ester derivatives can be used.

Suitable catalysts for performing the coupling reaction include, but are not limited to $PAL_3$, where L is any ligand normally associated with palladium. The preferred catalyst for the coupling reaction is Pd[P(pH)$_3$]$_3$. Catalysts including Pd[P(pH)$_3$]$_3$ Pd(OAc)$_2$ are also suitable for practicing the present invention. When Pd(P(pH)$_3$)$_3$ and Pd(OAc)$_2$ are employed together, the preferred molar ratio is about 3:1 Pd(P(pH)$_3$)$_3$ to Pd(OAc)$_2$. In a preferred embodiment, the catalyst also includes CUE. A preferred solvent for carrying out the coupling chemistry is THF. Preferably, the coupling chemistry is performed under an argon atmosphere, at temperatures between 0° C. and room temperature.

Modification of $R^1$ and $R^2$

The modifications of positions $R^{3-6}$ have been previously described in the literature. Additional modifications made possible by the present invention include modifications at positions $R^1$ and $R^2$. By modifying these positions, various functional groups can be incorporated into the nucleosides by adding the desired amine to the intermediate from step b using Michael addition chemistry (step c), described below.

When $R^1$ or $R^2$ is H, the compounds of the Formulae (III) or (IV) with a leaving group at the 5-position can undergo rearrangement to the compounds of Formula (V) or (VI) in a second Michael reaction. By choosing $R^1$ or $R^2$ as a group which is cleaved intracellularly (or in the nucleus of a cell) compounds can be prepared which incorporate into viral DNA or RNA, and then, as the $R^1$ or $R^2$ groups are cleaved intracellularly to H, subsequently rearrange to the urea derivatives. Such a rearrangement is capable of disrupting the genetic information of the pathogen. Groups capable of being cleaved intracellularly via enzymatic or other means include, but are not limited to,

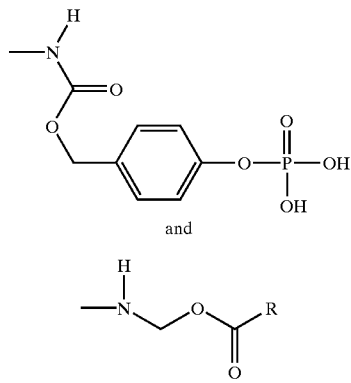

In an alternative embodiment, the hydroxy groups in the desired nucleoside derivatives can be protected with a tetraisopropyldisiloxyl (TIPS) group to gain access to "free" nucleoside analogs. These compounds undergo the above-described palladium catalyzed conversion in good yield to provide the TIPS protected intermediates.

When $R^1$ and $R^2$ are not H, i.e., in the case of tertiary amines, care must be taken when deprotecting isopropylidene ketals. Overly acidic conditions can cause inadvertent deglycosylation. This deglycosylation is not observed when one of $R^1$ and $R^2$ is H, i.e., in the case of secondary amines.

In an alternative embodiment, $R^1$ and $R^2$ can be chosen in such a way as to modulate, modify and/or control the biological activity of the compound. This can be achieved by adding a second biological activity to the compound, and/or enhancing the efficacy, bioavailability, potency, specificity and/or limits the toxicity of the compound. For example, choosing $R^1$ or $R^2$ to be an HIV aspartyl protease inhibitor and $R^5$ to be $N_3$ can provide a dual action antiviral for the treatment of HIV infection.

In addition, $R^1$ and $R^2$ can be chosen to increase either the lipophilicity or the hydrophilicity of the compounds in order to optimize their bioavailability.

Michael Addition Chemistry

Conditions for performing Michael addition reactions are well known to those of skill in the art. Any amine of the formula $HNR^1R^2$ can be added to the ene-one intermediates produced in step b, described above.

Interestingly, it has been observed that when pyrimidine nucleosides are modified in the 5-position with the ene-one moiety, and a primary amine is added to the ene-one in a first Michael addition reaction, a second Michael addition reaction with the ene-one or ene-imine in the pyrimidine ring is possible. Accordingly, the 5-position modified pyrimidine intermediate from the palladium coupling chemistry (step b) described above can be reacted with primary amines (as the free base or as the hydrochloride salt in the presence of an organic base) in a double Michael reaction to form urea nucleoside derivatives.

For reasons that are not yet fully understood, when a primary amine is added to a TIPS-protected 5-position modified pyrimidine intermediate, the second Michael reaction either does not occur or occurs slowly. If the TIPS group is removed in the presence of a base, the resulting deprotected compound undergoes the second Michael addition. If the deprotection occurs under pH neutral conditions (i.e., using a fluoride ion bound to a resin) the second Michael addition either does not occur or occurs very slowly.

Preparation of Oligonucleotides.

Oligonucleotides can be prepared using the modified nucleosides of the present invention, alone, or in combination with other modified nucleosides and/or naturally occurring nucleosides. The automated synthesis of oligodeoxynucleosides is routine practice in many laboratories (Matteucci, M. D. and Caruthers, M. H., *J. Am. Chem. Soc.*, 103:3185–3191 (1981), the contents of which are hereby incorporated by reference). Synthesis of oligoribonucleosides is also known (Scaringe, S. A., et al., *Nucleic Acids Res.*, 18:5433–5441 (1990), hereby incorporated by reference).

Representative modified nucleoside compounds of the present invention are shown in Tables I and II. Table I exemplifies compounds of the formula (III) wherein $R^1$–$R^6$ have the values indicated. Table II exemplifies compounds of the formula (V) wherein $R^1$–$R^6$ have the values indicated. These compounds can be converted to the corresponding cytidine derivatives (of Formulae IV and VI, respectively) using known methods.

TABLE I

| Cmpd. | $R^1$ | $R^2$ | $R^3$ | $R^4$ | $R^5$ | $R^6$ |
|---|---|---|---|---|---|---|
| 8 | $CH_2CO_2Et$ | $CH_3$ | H | | $OC(CH_3)_2O$ | OH |
| 9 | $CH(i-Pr)CO_2Et$ | $CH_3$ | H | | $OC(CH_3)_2O$ | OH |
| 10 | $CH(Bn)CO_2Et$ | $CH_3$ | H | | $OC(CH_3)_2O$ | OH |
| 11 | $CH_2CH_2(4$-imidazole) | $CH_3$ | H | | $OC(CH_3)_2O$ | OH |
| 14 | $CH(i-Pr)CO_2Et$ | H | H | OH | $OSi(i-Pr)_2OSi(i-Pr)_2O$ | |
| 15 | $CH(Bn)CO_2Et$ | H | H | OH | $OSi(i-Pr)_2OSi(i-Pr)_2O$ | |
| 16 | $CH(i-Pr)CO_2Et$ | H | H | OH | OH | OH |
| 17 | $CH(Bn)CO_2Et$ | H | H | OH | OH | OH |
| 20 | $CH(i-Pr)CO_2Et$ | $CH_3$ | H | OH | $OSi(i-Pr)_2OSi(i-Pr)_2O$ | |
| 21 | $CH(Bn)CO_2Et$ | $CH_3$ | H | OH | $OSi(i-Pr)_2OSi(i-Pr)_2O$ | |
| 22 | $CH(i-Pr)CO_2Et$ | $CH_3$ | H | OH | OH | OH |
| 23 | $CH(Bn)CO_2Et$ | $CH_3$ | H | OH | OH | OH |

TABLE II

| Cmpd. | $R^1$ | $R^3$ | $R^4$ | $R^5$ | $R^6$ |
|---|---|---|---|---|---|
| 3 | $CH_2CO_2Et$ | H | | $OC(CH_3)_2O$ | OH |
| 4 | $CH(i-Pr)CO_2Et$ | H | | $OC(CH_3)_2O$ | OH |
| 5 | $CH(Bn)CO_2Et$ | H | | $OC(CH_3)_2O$ | OH |
| 6 | $CH_2CH_2(4$-imidazole) | H | | $OC(CH_3)_2O$ | OH |
| 7 | $CH(CH_2OH)CH_2(4$-imidazole) | H | | $OC(CH_3)_2O$ | OH |
| 18 | $CH(i-Pr)CO_2Et$ | H | OH | OH | OH |
| 19 | $CH(Bn)CO_2Et$ | H | OH | OH | OH |

Specific non-limiting examples of the synthesis of modified nucleoside compounds of the present invention are illustrated below in Schemes II and III. For example, commercially available 5-iodouridine can be protected as the isopropylidene 1 which can then be treated with vinyltributyltin and carbon monoxide in the presence of a palladium catalyst to give 2 in high yield (Scheme II). Compound 2 is a key intermediate which can be used to synthesize a number of compounds of the invention. Treatment of 2 with primary amines (as the free base or as the hydrochloride salt in the presence of an organic base) leads to the formation of the urea nucleoside derivatives 3–7. The amine hydrochloride (or any other salt) can be used directly in the presence of an organic base such as triethylamine or, the free base of the amine can be generated separately by treating the amine salt with CaH$_2$ in DMF. Alternatively, secondary amines can be utilized to react with 2 to give the uridine derivatives 8–11.

Protection of 5-iodouridine with the tetraisopropyldisiloxyl TIPS) group can be utilized to gain access to the "free" nucleoside analogs (Scheme III). Treatment of 5-iodouridine with dichloro-tetraisopropyldisiloxane in DMF in the presence of imidazole provides the 3',-5'-TIPS derivative 12. Compound 12 undergoes the palladium catalyzed conversion in good yield to provide the TIPS protected intermediate 13. Reaction of 13 with primary amines gives the secondary amines 14–15 which can be deprotected with polymer-supported fluoride to provide the nucleosides 16–17. The derivatives 16–17 rearrange slowly to 18–19 upon treatment with triethylamine in DMSO. Compounds 18–19 can be synthesized directly from 14–15 by deprotection with triethylamine hydrofluoride effecting deprotection and rearrangement in one step. The intermediate 13 can be converted to the uridine analog 20–21 in the presence of secondary amines in a manner analogous to the previously described reactions of isopropylidene 2. Deprotection of 20–21 with either HF/triethylamine of polymer-supported fluoride provides the nucleosides 22–23 in high yield. It will be evident to those skilled in the art that each of the above mentioned reactions may require slightly different reaction and purification conditions in order to obtain optimized yields of the desired products.

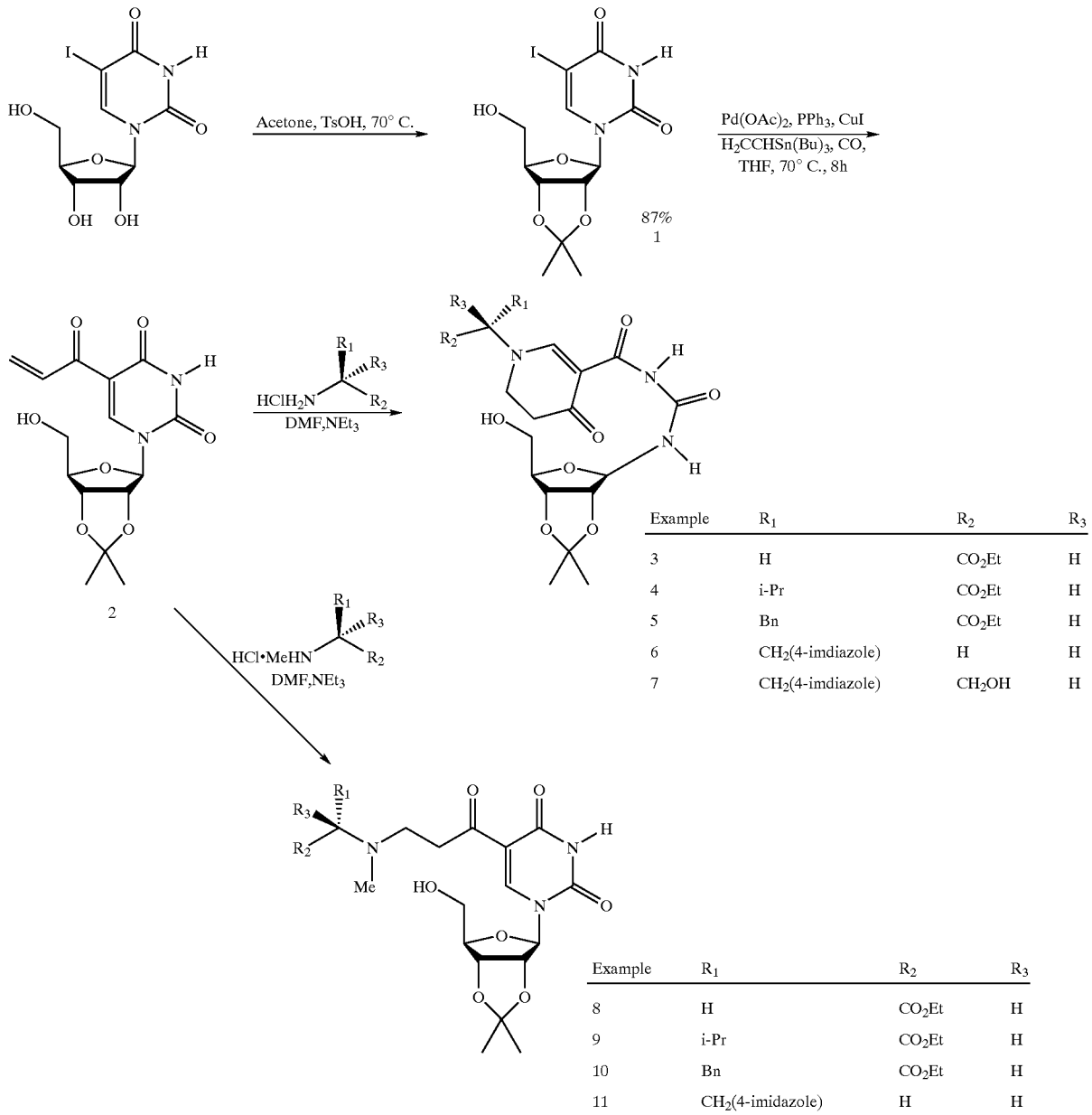

Scheme II

Scheme III
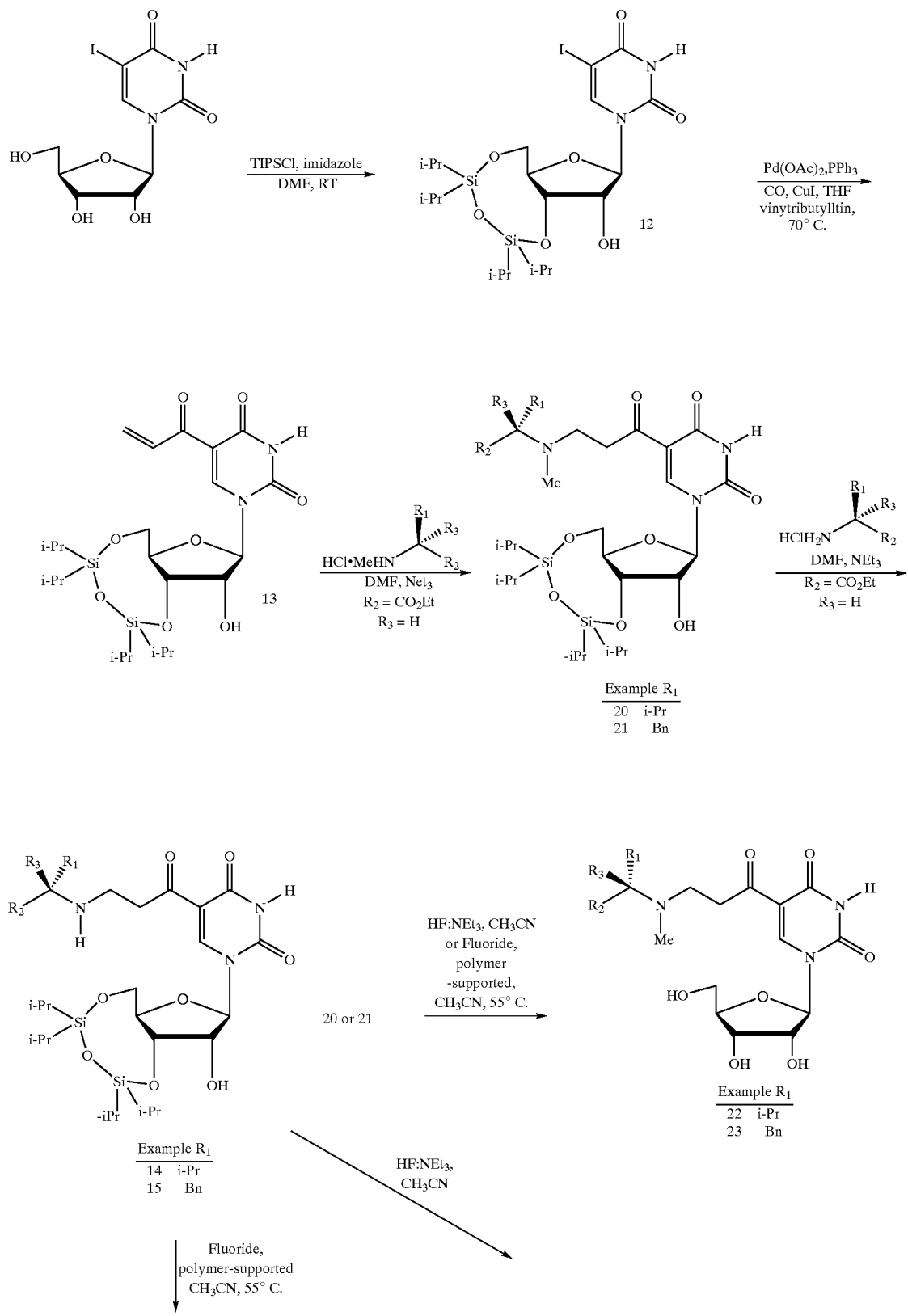

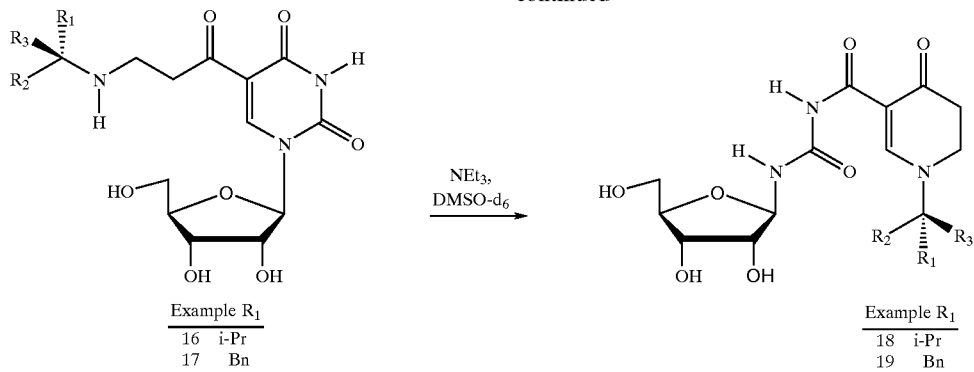

| Example | R₁ |
|---|---|
| 16 | i-Pr |
| 17 | Bn |

| Example | R₁ |
|---|---|
| 18 | i-Pr |
| 19 | Bn |

Methods of Using the Compounds

The modified nucleosides of the present invention may be useful therapeutically as anti-cancer, anti-bacterial or anti-viral drugs. The nucleosides may also be incorporated into DNA, which may be useful for diagnostic applications, as well as gene shuffling applications. The nucleosides can also be used, alone or in combination with other modified nucleosides and/or naturally occurring nucleosides, to prepare oligonucleotides.

Use as Antiviral Compounds

Several nucleosides are known to possess anti-viral activity. These are often modified nucleosides, where the modification is at the 2' or 3' positions. Modified nucleosides can inhibit viral replication by inhibiting viral thymidine kinase by slowing replication. Replication is slowed by reducing the amount of nucleotide monophosphates available. Alternatively, nucleoside analogs like acyclovir take advantage of the different specificity of the thymidine kinases, viral and human, by only being phosphorylated by the viral enzyme. The phosphorylated nucleoside is subsequently incorporated by the infected cells, resulting in chain termination and cell death. The nucleosides of the present invention can be modified to be phosphorylated by viral kinases, in preference to the human kinases, leading to specificity and reduced toxicity.

Modifications that result in increased specificity to viral kinases are well known to those of skill in the art. For example, the 3' position can be modified to contain an azide moiety, as in AZT. By incorporating known modifications to the nucleosides at the 2' and 3' positions ($R^3$–$R^5$), the modified nucleosides of the present invention are expected to also have anti-viral activity. In addition, modifying $R^1$ and $R^2$ on the amine can also provide anti-viral activity. For example, $R^2$ can be a proteinase inhibitor, and $R^5$ can be an azide, to provide a dual activity anti-viral compound. Alternatively, $R^2$ can be a moiety that is cleaved intracellularly, such that the virus incorporates the nucleoside, and when the moiety is cleaved intracellularly, the modified nucleoside disrupts viral replication. Methods for screening anti-viral activity are well known to those of skill in the art.

Use as Anticancer Drugs

The compounds of the present invention may have utility as anticancer drugs. As discussed above, the compound of the invention may incorporate into the DNA and disrupt replication of the cancer cells. Methods for screening anti-cancer activity are well known to those of skill in the art.

When administered as anti-cancer, anti-bacterial or anti-viral drugs, the compounds can be administered in a range of between approximately 0.5–98 mg nucleoside/m²/day, preferably between 15 and 25 mg nucleoside/m²/day. Preferred modes of administration include parental, intravenous, intramuscular, and oral. When administered via injection, the nucleosides can be dissolved in a pharmaceutically acceptable carrier, such as PBS, saline, and dextrose solutions. Typical concentrations range from between approximately 0.5 to 50 mg/nL solution, and more preferably, between approximately 1.0–25 mg/mL solution. The amount of nucleoside administered to a patient will be expected to vary according to the nature and severity of the disease to be treated, as will be judged by a physician of skill in the art.

Pre- and Post-SELEX Modification

The nucleosides of the present invention can be used to prepare oligonucleotides, either alone or in combination with other modified nucleosides and/or naturally occurring nucleosides. One problem associated with using naturally occurring nucleosides in therapeutic and in vivo diagnostic uses is that the oligonucleotides in their phosphodiester form may be quickly degraded in body fluids by intracellular and extracellular enzymes such as endonucleases and exonucleases before the desired effect is manifest. As discussed above, certain chemical modifications of the nucleosides increase the in vivo stability of the oligonucleotides. It is preferred that the nucleosides be modified in such a way as to provide increased in vivo stability.

When the nucleosides are used to prepare oligonucleotides according to the SELEX methodology, they can be used in both pre- and post-SELEX modification. Pre-SELEX modifications yield oligonucleotides with both specificity for their SELEX target and improved in vivo stability. Post-SELEX modifications made to nucleosides can result in improved in vivo stability without adversely affecting the binding or interacting capacity of the oligonucleotides.

Diagnostic Uses

When the nucleosides contain a radiolabel, a fluorescent tag such as rhodamine or fluorescein, or are biotinylated, they can be detected after the nucleoside is incorporated into DNA. These embodiments are particularly useful as in vivo or in vitro diagnostics. Oligonucleotides that include the modified nucleosides can also be labeled, and when they specifically bind to or interact with a target site, the binding or interaction can be observed by detecting the label. This can be useful as a diagnostic tool, to determine whether a particular binding site is present in a sample by adding a specific oligonucleotide that selectively binds to or interacts with the site, washing away unbound oligonucleotide, and observing binding or interaction by looking for the label.

As discussed below, the nucleosides can also be used as strand cleavage reagents for sequencing oligonucleotides. In this fashion, the nucleosides are not detected by radioactivity, but rather, by cleaving the target DNA in a predictable manner.

Use as Strand Cleavage Agents

The compounds of the invention are useful as strand cleavage reagents for sequencing oligonucleotides. The triphosphates of the 5-[($R^1R^2$)aminoethylcarbonyl] pyrimidine nucleosides (where one of $R^1$ or $R^2$ is a protective group which masks the amino group) are incorporated into DNA and/or RNA during enzyme catalyzed polymerase reactions. The full length oligonucleotide is then exposed to a reagent which removes the amine protective group thereby unmasking the amine. The intramolecular Michael addition reaction leads to the formation of a urea nucleoside derivative which is formally related to the urea nucleoside obtained from exposure of thymidine to hydrazine in the Maxam-Gilbert sequencing method. The urea nucleoside is then cleaved with piperidine which leads to strand cleavage via the known β-elimination mechanism of the Maxam-Gilbert method (Scheme IV). The compounds of the invention may be useful for cleaving large oligonucleotides into smaller fragments for sequencing or use in gene shuffling applications.

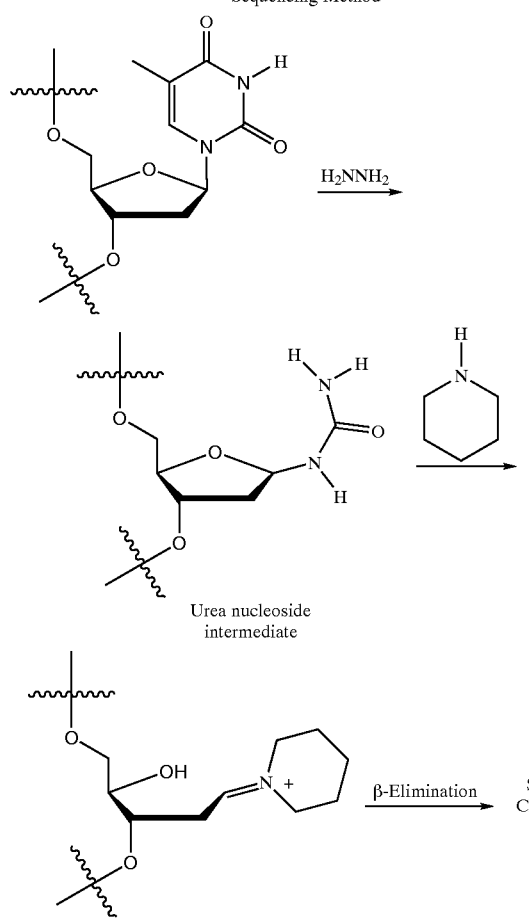

Scheme IV
Strand Cleavage At A Thymidine Residue In The Maxam-Gilbert Sequencing Method

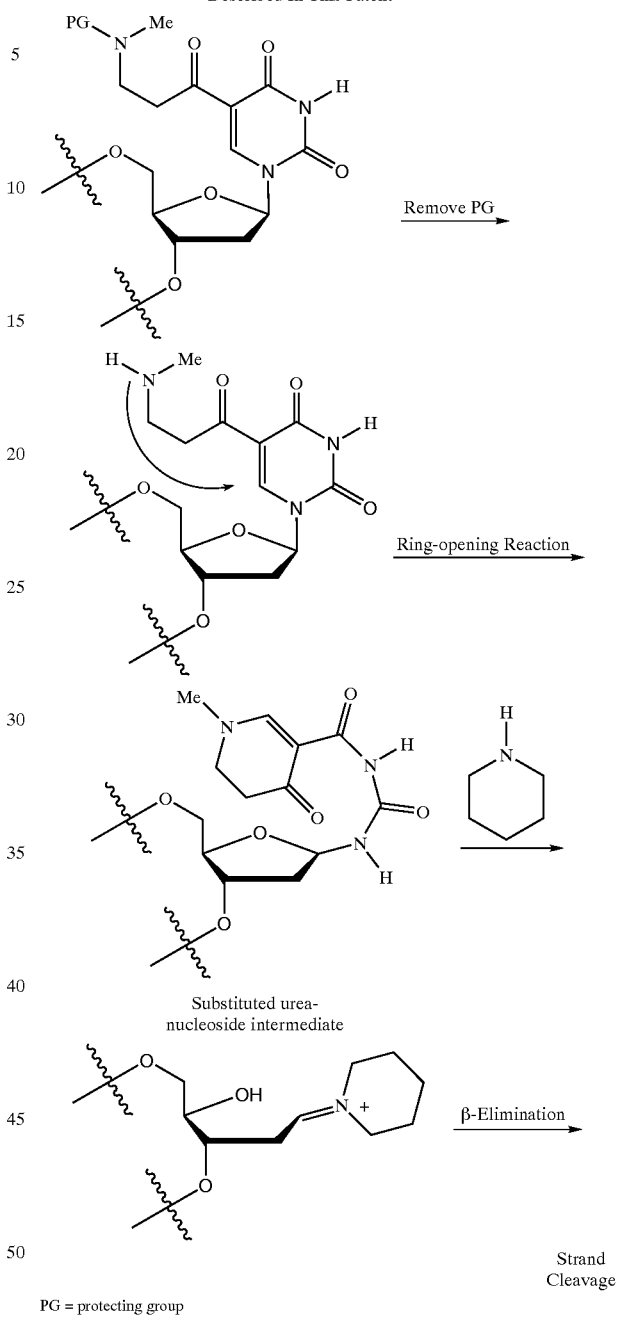

The following examples are given to explain and illustrate the present invention and are not to be taken as limiting the invention.

EXAMPLE 1

Synthesis of 5-Iodouridine-2',3'-isopropylidene (1)

A suspension of 5-iodouridine (10.0 g, 27 mmol), 0.5 g of toluenesulfonic acid and 600 ml of acetone was heated to 70° C. The refluxing acetone was passed through an addition funnel packed with 4 Å molecular sieves. After 4 hours the reaction was judged complete by TLC (silica gel, 9:1 $CHCl_3/MeOH$). The reaction volume was reduced to approximately 150 mL and the resulting mixture passed through a 125 mL pad of flash silica gel. The product was eluted from the silica with about 500 mL of acetone. The resulting solution was concentrated to a white solid which was crystallized from 225 mL of absolute ethanol to give 9.59 g (87%) of the product as a white crystalline solid. $^1$H NMR (d$_6$-DMSO) δ 1.28 (s, 3H), 1.48 (s, 3H), 3.56 (ddd, 1H, J=4.0, 4.9, 11.8 Hz), 3.61 (ddd, 1H, J=4.0, 4.5, 11.8 Hz), 4.09 (dt, 1H, J=3.7, 4.0 Hz), 4.75 (dd, 1H, J=3.5, 6.3 Hz), 4.92 (dd, 1H, J=2.5, 6.3 Hz), 5.20 (t, 1H, J=5.1 Hz), 5.82 (d, 1H, J=2.4 Hz), 8.33 (s, 1H), 11.76 (br s, 1H); $^{13}$C NMR (d$_6$-DMSO) δ 25.09, 26.93, 61.04, 69.49, 80.22, 83.84, 86.87, 91.29, 112.83, 146.09, 150.01, 160.55; IR (KBr, diffuse reflectance accessory) ν$_{max}$ 3428, 3232, 1707, 1662, 1605, 1454, 1270, 1114, 854, 786, 629 cm$^{-1}$.

EXAMPLE 2

Synthesis of 5-(1'-propenoyl)uridine-2',3'-isopropylidene (2)

Compound 1 (4.10 g, 10 mmol), palladium(II)acetate (449 mg, 2.0 mmol), copper(I)iodide (1.14 g, 6.0 mmol) and triphenylphosphine (1.57 g, 6.0 mmol) were loaded into a 1 L capacity reaction flask with a self-contained pressure apparatus. The apparatus was purged with argon and 150 mL of dry, freshly distilled THF added to the reaction flask. The addition funnel of the apparatus was charged with a solution of vinyltributyltin (4.76 g, 15 mmol) in 200 mL of dry THF. The entire apparatus was evacuated and charged with argon three times and then with carbon monoxide at 55 psi three times. After the last evacuation cycle the vessel was pressurized to 55 psi with carbon monoxide and sealed. The reaction flask was lowered into an oil bath at 70° C. and vigorous stirring initiated. After 30 minutes, slow dropwise addition of the vinyltin solution was started and continued over 6 hours. After the addition was complete, the mixture was stirred for an additional 4 hours until a black soot had formed. The vessel was removed from the oil bath, cooled, degassed slowly and evacuated with a water aspirator. The mixture was filtered, concentrated and the residue dissolved in 50 mL of CH$_2$Cl$_2$ and filtered through Hyflo. After concentrating to approximately 25 mL, the filtrate was added dropwise to 300 mL of hexane. The precipitated crude product (2.86 g, 85%) was filtered and dried under vacuum. The product was purified further by flash chromatography (0.5 to 5.0% MeOH/CHCl$_3$) to give a yellow solid: $^1$H NMR (d$_6$-DMSO) δ 1.28 (s, 3H), 1.48 (s, 3H), 3.52–3.64 (m, 2H), 4.23 (dt, 1H, J=3.1, 3.9 Hz), 4.75 (dd, 1H, J=2.9, 6.2 Hz), 4.94 (dd, 1H, J=2.1, 6.2 Hz), 5.15 (t, 1H, J=4.7 Hz), 5.78 (dd, 1H, J=2.2, 10.4 Hz), 5.85 (d, 1H, J=2.1 Hz), 6.25 (dd, 1H, J=2.1, 17.2 Hz), 7.44 (dd, 1H, J=10.3, 17.2 Hz), 8.64 (s, 1H), 11.76 (br s, 1H); $^{13}$C NMR (d$_6$-DMSO) δ 25.01, 26.87. 61.14, 80.60, 84.58, 87.66, 93.07, 111.23, 112.49, 128.13, 134.60, 148.84, 149.53, 161.37, 184.98; IR (KBr, film) ν$_{max}$ 1694 cm$^{-1}$.

EXAMPLE 3

Synthesis of Compound 3

Glycine ethyl ester hydrochloride (167 mg, 1.2 mmol) was dissolved in 1 mL of dry DMF and treated with calcium hydride (27 mg, 0.65 mmol). After standing overnight, the mixture was filtered through a plug of glass wool into a solution of compound 2 (338 mg, 1.0 mmol) in 1 mL of dry DMF. The reaction was allowed to proceed for 48 hours and then the reaction mixture was concentrated and co-evaporated from absolute ethanol three times. The residue was chromatographed on flash silica gel (1–5% MeOH/CHCl$_3$) to give 82 mg (19%) of compound 3: $^1$H NMR (CDCl$_3$) δ 1.32 (t, 3H, J=7.4 Hz), 1.35 (s, 3H), 1.56 (s, 3H), 2.61–2.67 (m, 2H), 3.62–3.81 (m, 3H), 3.90 (dd, 1H, J=1.8, 12.0 Hz), 4.19 (d, 1H, J=18 Hz), 4.25 (q, 1H, J=7.1 Hz), 4.26 (q, 1H, J=7.1 Hz), 4.32 (br s, 1H), 4.26–4.60 (br, —OH), 4.66 (d, 1H, J=18 Hz), 4.70 (dd, 1H, J=1.7, 6.0 Hz), 4.91 (d, 1H, J=6.0 Hz), 5.88 (dd, 1H, J=1.7, 10.1 Hz), 8.15 (s, 1H), 9.23 (d, 1H, J=10.1 Hz), 11.09 (br s, 1H); $^{13}$C NMR (CDCl$_3$) δ 14.11, 25.04, 26.81, 34.62, 47.78, 57.51, 62.10, 63.51, 82.63, 86.17, 88.17, 99.99, 112.42, 153.30, 160.47, 165.45, 168.00, 189.58; IR (KBr, film) ν$_{max}$ 3424(br), 3264(br), 2985, 2938, 1744, 1665(s), 1593(s), 1206(s), 1096(s) cm$^{-1}$.

EXAMPLE 4

Synthesis of Compound 4

L-Valine ethyl ester hydrochloride (218 mg, 1.2 mmol) was dissolved in 1 mL of dry DMF and treated with calcium hydride (27 mg, 0.65 mmol) overnight. The mixture was filtered through a plug of glass wool into a solution of compound 2 in 1 mL of dry DMF and the reaction allowed to stand at room temperature for 24 hours. The reaction mixture was concentrated and co-evaporated from absolute ethanol two times. Trituration with ether gave a granular solid which was chromatographed on flash silica gel (1–3% MeOH/CHCl$_3$) to give 166 mg (34%) of compound 4: $^1$H NMR (CDCl$_3$) δ 0.98 (d, 3H, J=6.7 Hz), 1.02 (d, 3H, J=6.6 Hz), 1.34 (s, 3H), 1.35 (dd, 3H, J=7.1, 7.2 Hz), 1.55 (s, 3H), 2.31 (dheptet, 1H, J=6.6, 10.0 Hz), 2.42–2.52 (m, 1H), 2.67–2.79 (m, 1H), 3.50–3.61 (m, 1H), 3.75 (dd, 1H, J=2.7, 11.9 Hz), 3.90 (dd, 1H, J=2.2, 11.9 Hz), 3.95 (d, 1H, J=10.0 Hz), 4.0–4.5 (br, —OH), 4.02–4.11 (m, 1H), 4.27 (dq, 1H, J=7.3, 10.9 Hz), 4.28–4.37 (m, 1H), 4.33 (dq, 1H, J=7.2, 10.7 Hz), 4.73 (dd, 1H, J=1.9, 6.1 Hz), 4.89 (dd, 1H, J=1.6, 6.1 Hz), 5.78 (dd, 1H, J=1.9, 9.3 Hz), 8.32 (s, 1H, 9.25 (d, 1H, J=9.4 Hz), 11.00 (br s, 1H); $^{13}$C NMR (CDCl$_3$) δ 14.05, 18.99, 19.47, 25.11, 26.84, 28.88, 34.75, 44.24, 61.82, 63.41, 74.24, 82.00, 85.95, 87.97, 100.37, 112.58.

EXAMPLE 5

Synthesis of Compound 5

L-Phenylalanine ethyl ester hydrochloride (276 mg, 1.2 mmol) was dissolved in 1 mL of dry DMF and treated with calcium hydride (27 mg, 0.65 mmol) overnight. The mixture was filtered through a plug of glass wool into a solution of compound 2 (338 mg, 1.0 mmol) and the reaction allowed to proceed at room temperature for 24 hours and then 80° C. for 3 hours. The reaction mixture was concentrated and co-evaporated from absolute ethanol three times to give a granular solid. The solid was chromatographed on flash silica gel (1–3% MeOH/CHCl$_3$) to give 172 mg (32%) of compound 5 as a white solid: $^1$H NMR (CDCl$_3$) δ 1.34 (s, 3H), 1.34 (t, 3H, J=7.2 Hz), 1.55 (s, 3H), 2.35 (ddd, 1H, J=5.6,11.2, 16.7 Hz), 2.69 (ddd, 1H, J=6.2, 12.5, 16.7 Hz), 3.03 (dd, 1H, J=11.1, 14.5 Hz). 3.33–3.54 (m, 2H), 3.81 –3.90 (m, 1H), 3.75–4.10 (br, —OH), 4.25–4.37 (m, 3H), 4,69 (dd, 1H, J=2.4, 6.1 Hz), 4.70 (d, 1H, J=14.6 Hz), 4.88 (dd, 1H, J=1.4, 6.1 Hz), 5.74 (dd, 1H, J=2.2, 9.4 Hz), 7.14–7.33 (m, 5H, ArH), 7.98 (s, 1H), 9.12 (d, 1H, J=9.4 Hz), 10.93 (s, 1H).

EXAMPLE6

Synthesis of Compound 6

A solution of histamine (111 mg, 1.0 mmol) in 1 mL of dry DMF was added to a solution of compound 2 (338 mg, 1 mmol) in 1 mL of dry DMF. After standing at room temperature overnight, the dark green solution was concentrated and the residue triturated with ether to give 446 mg of a light green solid. The solid was chromatographed on flash silica gel (20% saturated methanolic ammonia/THF) to give compound 6: $^1$H NMR (DMSO-d$_6$) δ 1.26 (s, 3H), 1.43 (s, 3H), 2.47 (t, 2H, J=7.7 Hz), 2.50–2.95 (m, 2H), 3.31–3.62 (m, 2H), 3.67 (t, 2H, J=7.8 Hz), 3.81 (m, 2H), 4.06 (br m, 1H), 4.56 (dd, 1H, J=1.9, 6.1 Hz), 4.72 (d, 1H, J=6.1 Hz), 5.15 (t, 1H, J =4.4 Hz), 5.53 (dd, 1H, J =1.8, 9.5 Hz), 7.57 (s, 1H), 8.07 (br s, 1H), 9.26 (d, 1H, J=9.5 Hz), 11.03 (s, 1H), 11.85 (br s, 1H).

EXAMPLE 7

Synthesis of Compound 7

The general procedure of examples 1–5 was followed for the synthesis of compound 7 using histidinol dihydrochloride as the amine component. The purification procedure of example 6 was utilized for the chromatographic separation.

EXAMPLE 8

Synthesis of Compound 8

Sarcosine ethyl ester hydrochloride (154 mg, 1.0 mmol) was suspended in 1 mL of dry DMF and 111 mg (1.1 equiv.) of triethylamine added. Compound 2 (338 mg, 1.0 mmol) was added as a solid and the mixture was allowed to stand overnight. The reaction mixture was quenched with 10 mL of water, extracted with chloroform (3×10 mL) and the combined chloroform layers dried over sodium sulfate. The filtered solution was concentrated and co-evaporated 4 times from absolute ethanol to give 423 mg (95%) of compound 8 as a white foam: $^1$H NMR (CDCl$_3$) δ 1.27 (t, 3H, J=7.1 Hz), 1.36 (s, 3H), 1.58 (s, 3H), 2.37 (s, 3H), 2.82–2.90 (m, 2H), 3.07 (dt, 1H, J=6.9, 16.8 Hz), 3.21–3.34 (m, 3H), 3.84 (dd, 1H, J=3.0, 11.9 Hz), 3.96 (dd, 1H, J=2.2, 6.2 Hz), 4.17(q, 2H, J=7.1 Hz), 4.46–4.47(m, 1H), 4.91(dd, 1H, J=2.0, 6.2 Hz), 4.95 (dd, 1H, J=2.3, 6.2 Hz), 5.83 (d, 1H, J=2.3 Hz), 8.66 (s, 1H); $^{13}$C NMR (CDCl$_3$) δ 14.18, 25.14, 27.07, 39.96, 42.25, 51.65, 58.11, 60.63, 62.47, 81.03, 85.27, 87.99, 95.57, 111.35, 113.77, 149.03, 149.67, 161.16, 170.89, 195.37; IR (KBr, film) ν$_{max}$ 3493, 3225, 3068, 2986, 2934, 2834, 1727(s), 1698(s), 1592(m), 1456(m), 1384, 1282, 1212(m), 1104(m), 1069(m), 853, 798, 733, 580 cm$^{-1}$.

EXAMPLE 9

Synthesis of Compound 9

Compound 9 was synthesized according to the procedure described in Example 8 using N-methyl-L-valine ethyl ester hydrochloride (196 mg, 1.0 mmol). After work-up the product was co-evaporated from absolute ethanol 5 times to give 448 mg (90%) of compound 9 as a white solid after drying under vacuum: $^1$H NMR (CDCl$_3$) δ 0.85 (d, 3H, J=6.5 Hz), 0.89 (d, 3H, J=6.6 Hz), 1.27 (t, 3H, J=7.1 Hz), 1.93–2.09 (m, 1H), 2.28 (s, 3H), 2.73–2.82 (m, 2H), 2.86–2.96 (m, 1H), 3.08–3.34 (m., 2H), 3.83 (dd, 1H, J=3.0, 11.8Hz), 3.97 (dd, 1H, J=2.1, 11.8 Hz), 4.17 (q, 2H,J=7.1 Hz), 4.42 (br m, 1H), 4.91–4.97 (br m, 2H), 5.80 (d, 1H, J=2.0 Hz), 8.57 (s, 1H); $^{13}$C NMR (CDCl$_3$) δ 14.59, 19.39, 19.64, 25.17, 27.14, 27.29, 37.50, 41.09, 49.59, 59.76, 62.58, 73.48, 80.75, 84.66, 87.41, 95.66, 112.27, 114.20, 148.91, 149.62, 160.89, 171.88, 195.89; IR (KBr, film) ν$_{max}$ 3491, 3216, 3067, 2981(m), 1723(s), 1698(s), 1594(m), 1459(m), 1384, 1280, 1241, 1181, 1157, 1104(m), 1027, 914, 825, 787, 732 cm$^{-1}$.

EXAMPLE 10

Synthesis of Compound 10

Compound 10 was synthesized according to the general procedure described in Example 8 using N-methyl-L-phenylalanine ethyl ester hydrochloride (244 mg, 1.0 mmol). The product was co-evaporated from absolute ethanol 7 times and dried under vacuum to give 510 mg (93%) of compound 10 as a white solid: $^1$H NMR (CDCl$_3$) δ 1.14 (t, 3H, J=7.1 Hz), 1.37 (s, 3H), 1.59 (s, 3H), 2.41 (s, 3H), 2.86–3.07 (m, 4H), 3.08–3.24 (m, 2H), 3.55 (dd, 1H, J=6.4, 8.7Hz), 3.82 (dd, 1H, J=3.0, 11.9 Hz), 3.96 (dd, 1H, J=2.1, 11.9 Hz), 4.06 (q, 2H, J =7.2 Hz), 4.42–4.43 (br m, 1H), 4.92 (dd, 1H, J=2.2, 6.2 Hz), 4.96 (dd, 1H, J=2.4, 6.3 Hz), 5.78 (d, 1H, J=2.3 Hz), 7.15–7.27 (m, 5H, ArH), 8.51 (s, 1H); $^{13}$C NMR (CDCl$_3$) δ 14.28, 25.17, 27.14, 35.74, 38.17, 40.66, 49.39, 60.24, 62.56, 68.32, 80.81, 84.73, 87.59, 95.86, 111.90, 114.12, 126.22, 128.19, 129.25, 138.21, 149.05, 149.58, 160.90, 171.78, 195.49; IR(KBr, film) ν$_{max}$ 3468, 3212, 3063, 2985(m), 2931, 1725(s), 1698(s), 1593(m), 1456(m), 1384, 1281, 1242, 1214, 1158, 1103(m,), 1073(m), 912, 853, 733(m), 701, 580 cm$^{-1}$.

EXAMPLE 11

Synthesis of Compound 11

The general procedure of Example 8 was followed using 100 mg of histamine dihydrochloride (100 mg, 0.5 mmol) and compound 2 (169 mg, 0.5 mmol) in 1 mL of dry DMF containing triethylamine (111 mg, 1.1 mmol).

EXAMPLE 12

Synthesis of Compound 12

A solution of 5-iodouridine (11.84 g, 32 mmol) and imidazole (9.60 g, 141 mmol) dissolved in 64 mL of dry DMF was treated with dichlorotetraisopropyldisiloxane (11.36 g, 36 mmol) and the resulting mixture stirred at room temperature overnight. The reaction mixture was concentrated under vacuum (40° C. bath) to a clear oil which was treated with 50 mL of 0.05 N HCl. The mixture was extracted with 250 mL of CH$_2$Cl$_2$ and then 50 mL of CH$_2$Cl$_2$. The combined extracts were dried over sodium sulfate and concentrated. The residue was co-evaporated from absolute ethanol 4 times and chromatographed on flash silica gel (1–2% MeOH/CHCl$_3$) to give 18.85 g (96%) of compound 12 as a white solid: $^1$H NMR (d$_6$-DMSO) δ 0.96–1.09 (m, 28H), 3.88–4.00 (m, 2H), 4.12–4.19 (m, 3H), 5.50–5.54 (m,2H), 7.95 (s, 1H), 11.73 (br s, 1H); $^{13}$C NMR (d$_6$-DMSO) δ 11.88, 12.13, 12.36, 12.73, 16.73, 16.82, 16.92(2x), 17.06, 17.28, 17.46, 17.56, 59.77, 69.41, 69.13, 73.22, 80.95, 90.88, 143.82, 149.85, 160.58.

EXAMPLE 13

Synthesis of Compound 13

Compound 12 (6.12 g, 10 mmol), palladium(II)acetate (337 mg, 1.5 mmol), copper(I)iodide (857 mg, 4.5 mmol) and triphenylphosphine (1.18 g, 4.5 mmol) were loaded into the 1L reaction flask of a pressure vessel and 150 mL of freshly distilled, dry THF added under an argon atmosphere. A solution of vinyltributyltin (4.76 g, 15 mmol) in 200 mL of dry THF was added to the attached addition funnel maintaining a positive argon pressure. The entire apparatus was evacuated and pressurized to 55 psi with carbon monoxide gas 4 times. The reactor was sealed at 55 psi and the reaction flask immersed in an oil bath preheated to 70° C. After stirring for 10 minutes, slow addition of the vinyltin solution was started and continued for 6 hours. Once the addition was complete the reaction was allowed to continue for another 15 minutes then removed from the oil bath. The CO pressure was released slowly and the entire apparatus was evacuated with a water aspirator. The deep red solution was stored in the freezer overnight and changed to a clear yellow upon standing. The mixture was concentrated to near dryness and chromatographed on flash silica gel (1–3% MeOH/CHCl$_3$) to give 2.0 g (37%) of compound 13 as a yellow foam: $^1$H NMR (CDCl$_3$) δ 1.00–1.09 (br m, 28H), 3.20 (br, 1H), 4.03 (dd, 1H, J=2.9, 12.3 Hz), 4.07–4.12 (m, 1H), 4.18 (dd, 1H, J=3.5, 12.4 Hz), 4.28 (d, 1H, J=5.6 Hz), 4.46–4.51 (m, 1H), 5.72 (d, 1H, J=1.2 Hz), 5.77 (dd, 1H, J=1.9, 10.4 Hz), 6.44 (dd, 1H, J=1.9, 17.1 Hz), 7.54 (dd, 1H, J=10.3, 17.1 Hz), 8.53 (s, 1H),~9.4 (br, 1H); $^{13}$C NMR (CDCl$_3$) δ 12.54, 12.59, 13.00, 13.36, 16.88, 16.96, 16.99 (2X), 17.09, 17.13, 17.26, 17.42, 60.99, 69.78, 74.74, 82.75, 92.47, 112.46, 129.30, 134.17, 148.23, 149.20, 161.07, 184.83.

EXAMPLES 14–23

Compounds 14, 15, 20 and 21 and their deprotection compounds 14, 15, 20 and 21 were synthesized using the methods described for compounds 9 and 10. The products were treated with HF/triethylamine in acetonitrile to give compounds 18,19,22 and 23, respectively. Treatment of compounds 14 and 15 with polymer-supported fluoride at 55° C. in acetonitrile provided compounds 16 and 17, respectively.

The invention has been described with respect to its preferred embodiments. It will be readily apparent to those skill in the art that further changes and modifications in the actual implementation of the concepts described herein can easily be made without departing from the spirit and scope of the invention as defined by the following claims.

We claim:

1. A method for preparing modified nucleosides, comprising:

a) reacting a nucleoside starting material having the following formula:

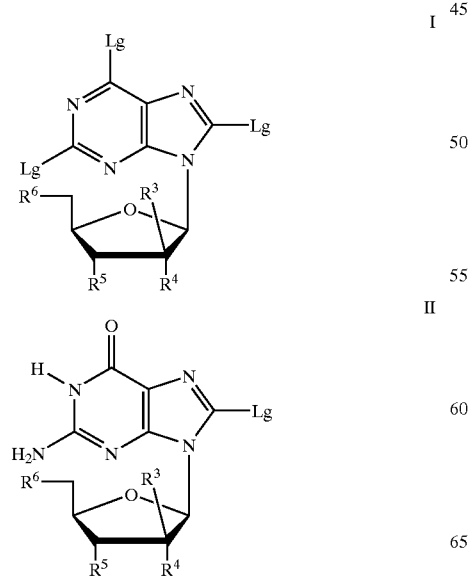

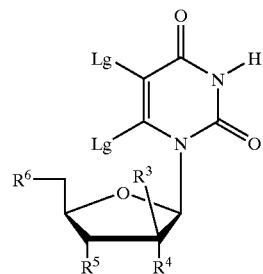

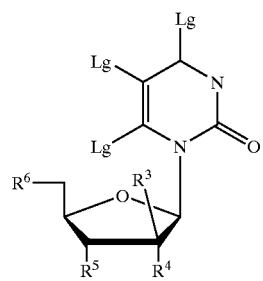

with a vinylstannane of the formula (alkyl$_3$Sn)(R$^8$)C=C(R$^8$)$_2$ and carbon monoxide in the presence of a palladium catalyst to form an ene-one intermediate;

b) reacting the ene-one intermediate with an amine of the formula HNR$^1$R$^2$ wherein:

Lg is independently selected from the group consisting of H or a leaving group;

R$^1$ and R$^2$ function to modulate, modify and/or control the biological activity of the compound and are independently selected from the group consisting of H, C$_1$–C$_{18}$ alkyl, alkenyl or alkynyl, phenyl, aralkyl, alkaryl, an alkanoic acid or its ester and amide derivatives, a peptide fragment, an HIV aspartyl protease inhibitor, groups that are cleaved intracellularly, and groups that increase the hydrophilicity, hydrophobicity, electrostatic capacity or hydrogen bonding capacity of the compound;

R$^3$, R$^4$ and R$^5$ are independently selected from the group consisting of H, —OH, protected oxy-, —NH$_2$, F, —N$_3$, —CN, —NC, —OAc, —SAc, —OBz, and —OSiR$^7$$_3$, wherein R$^7$ is C1–C4 alkyl or phenyl;

R$^6$ is selected from the group consisting of—OH, protected oxy-, phosphate, diphosphate, triphosphate, phosphate esters, phosphoramidites, phosphorothionates, and phosphorodithionates;

R$^8$ is independently selected from the group consisting of H, aryl, aralkyl, alkyl, alkaryl, alkenyl, alkynyl, alkoxy, and —C(O)—R$^9$, where R$^9$ is selected from the group consisting of H, alkyl, aryl, aralkyl, alkaryl and alkoxy;

the protected oxy- groups of R$^4$ and R$^5$ taken together can represent an isopropylidene group (—OC(CH$_3$)$_2$O—) or an orthoformate group (—OCH(OR$^7$)O—); and the protected oxy- groups of R$^5$ and R$^6$ taken together can represent a 3',-5'-tetraalkyldisiloxane group (—OSi(alkyl)$_2$OSi(alkyl)$_2$O—); and c) isolating said modified nucleoside.

2. A method for preparing modified nucleosides, comprising:

a) reacting a nucleoside starting material having the following formula:

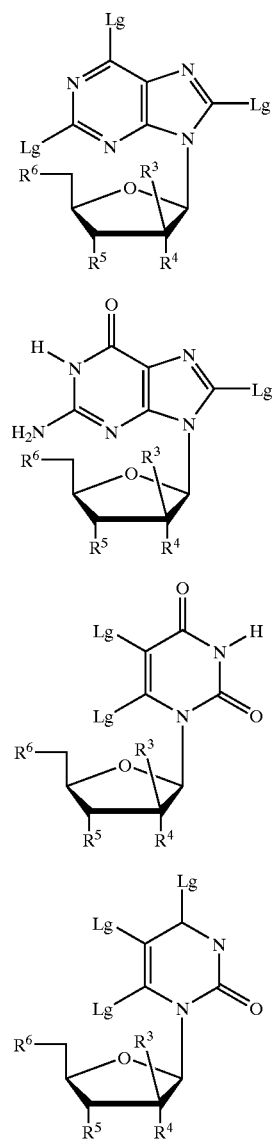

b) reacting the ene-one intermediate with an amine of the formula $HNR^1R^2$ wherein:

Lg is independently selected from the group consisting of H or a leaving group;

$R^1$ and $R^2$ are independently selected from the group consisting of H, $C_1$–$C_{18}$ alkyl, alkenyl or alkynyl, phenyl, aralkyl, alkaryl, an alkanoic acid or its ester and amide derivatives, a peptide fragment, an HIV aspartyl protease inhibitor, groups that are cleaved intracellularly, and groups that increase the hydrophilicity, hydrophobicity, electrostatic capacity or hydrogen bonding capacity of the compound;

$R^3$, $R^4$ and $R^5$ are independently selected from the group consisting of H, —OH, protected oxy-, —$NH_2$, F, —$N_3$, —CN, —NC, —OAc, —SAc, —OBz, and —$OSiR^7{}_3$, wherein $R^7$ is $C_1$–$C_4$ alkyl or phenyl;

$R^6$ is selected from the group consisting of —OH, protected oxy-, phosphate, diphosphate, triphosphate, phosphate esters, phosphoramidites, phosphorothionates, and phosphorodithionates;

$R^8$ is independently selected from the group consisting of H, aryl, aralkyl, alkyl, alkaryl, alkenyl, alkynyl, alkoxy, and —C(O)-$R^9$, where $R^9$ is selected from the group consisting of H, alkyl, aryl, aralkyl, alkaryl and alkoxy;

the protected oxy- groups of $R^4$ and $R^5$ taken together can represent an isopropylidene group (—OC($CH_3$)$_2$O—) or an orthoformate group (—OCH($OR^7$)O—); and the protected oxy- groups of $R^5$ and $R^6$ taken together can represent a 3',-5'-tetraalkyldisiloxane group (—OSi(alkyl)$_2$OSi(alkyl)$_2$O—); and wherein $R^3$–$R^6$ function to impart a first biological activity and $R^1$ or $R^2$ function to impart a second biological activity to the compound; and c) isolating said modified nucleoside.

3. A method for preparing modified nucleosides, comprising:

a) reacting a nucleoside starting material having the following formula:

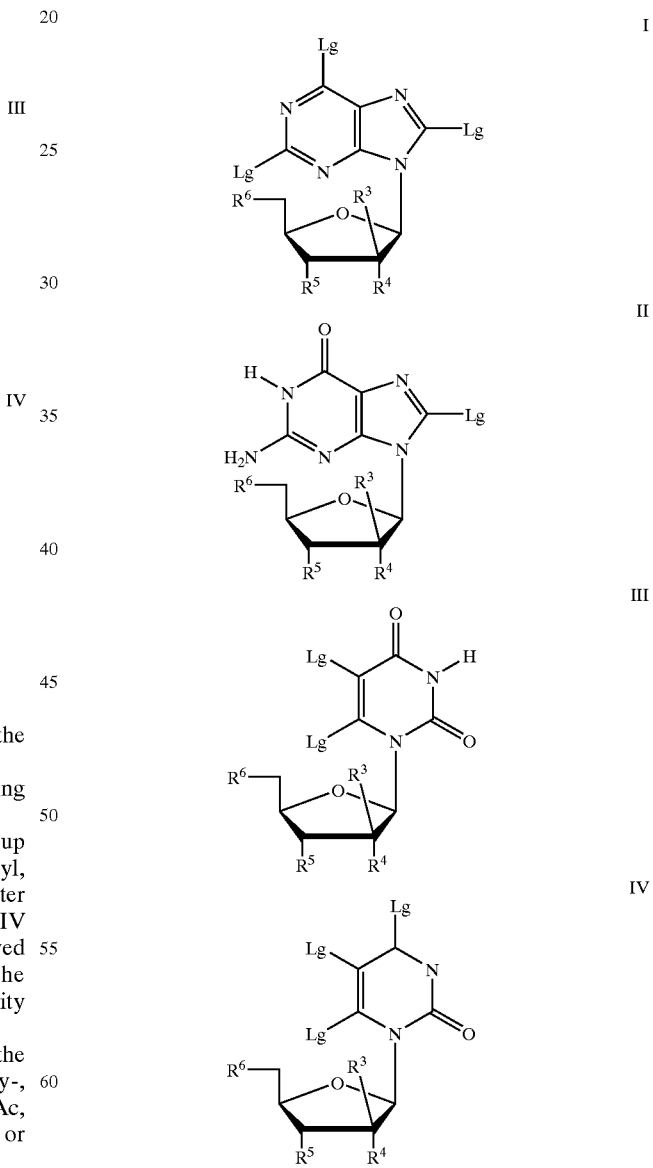

with a vinylstannane of the formula $(alkyl_3Sn)(R^8)C=C(R^8)_2$ and carbon monoxide in the presence of a palladium catalyst to form an ene-one intermediate;

b) reacting the ene-one intermediate with an amine of the formula $HNR^1 R^2$ wherein:
  Lg is independently selected from the group consisting of H or a leaving group;
  $R^1$ and $R^2$ function to enhance the efficacy, bioavailability, potency, specificity and/or limits the toxicity of the compound and are independently selected from the group consisting of H, $C_1$–$C_{18}$ alkyl, alkenyl or alkynyl, phenyl, aralkyl, alkaryl, an alkanoic acid or its ester and amide derivatives, a peptide fragment, an HIV aspartyl protease inhibitor, groups that are cleaved intracellularly, and groups that increase the hydrophilicity, hydrophobicity, electrostatic capacity or hydrogen bonding capacity of the compound;
  $R^3$, $R^4$ and $R^5$ are independently selected from the group consisting of H, —OH, protected oxy-, —NH$_2$, F, —N$_3$, —CN, —NC, —OAc, —SAc, —OBz, and —OSiR$^7{}_3$, wherein $R^7$ is $C_1$–C4 alkyl or phenyl;
  $R^6$ is selected from the group consisting of —OH, protected oxy-, phosphates diphosphate, triphosphate, phosphate esters, phosphoramidites, phosphorothionates, and phosphorodithionates;
  $R^8$ is independently selected from the group consisting of H, aryl, aralkyl, alkyl, alkaryl, alkenyl, alkynyl, alkoxy, and —C(O)—$R^9$, where $R^9$ is selected from the group consisting of H, alkyl, aryl, aralkyl, alkaryl and alkoxy;
  the protected oxy- groups of $R^4$ and $R^5$ taken together can represent an isopropylidene group (—OC(CH$_3$)$_2$O—) or an orthoformate group (—OCH(OR$^7$)O—); and
  the protected oxy- groups of $R^5$ and $R^6$ taken together can represent a 3',-5'-tetraalkyldisiloxane group (—OSi(alkyl)$_2$OSi(alkyl)$_2$O—); and
c)i isolating said modified nucleoside.

* * * * *